United States Patent
Yatscoff et al.

(12) 
(10) Patent No.: US 6,709,873 B1
(45) Date of Patent: Mar. 23, 2004

(54) METHOD FOR PRODUCTION OF ANTIBODIES TO SPECIFIC SITES OF RAPAMYCIN

(75) Inventors: Randall W. Yatscoff, Edmonton (CA); Andrew J. Malcolm, Edmonton (CA); Selvaraj Naicker, Edmonton (CA)

(73) Assignee: Isodiagnostika Inc., Edmonton (CA)

( * ) Notice: Subject to any disclaimer, the term of this patent is extended or adjusted under 35 U.S.C. 154(b) by 0 days.

(21) Appl. No.: 09/638,900

(22) Filed: Aug. 15, 2000

Related U.S. Application Data

(62) Division of application No. 09/419,877, filed on Oct. 15, 1999, which is a continuation-in-part of application No. 09/325,994, filed on Jun. 4, 1999, now abandoned, which is a continuation of application No. 09/101,309, filed as application No. PCT/CA98/00361 on Apr. 9, 1998, now abandoned.

(60) Provisional application No. 60/043,215, filed on Apr. 9, 1997.

(51) Int. Cl.[7] .................. G01N 33/53; C12P 21/04; C07K 16/00
(52) U.S. Cl. .................. 436/547; 436/548; 435/70.21; 435/70.2; 435/70.1; 530/388.9; 530/388.1
(58) Field of Search .................. 436/547, 548; 435/70.21, 70.2, 70.1; 530/388.9, 806, 350, 300, 317, 388.1, 387.1; 424/175.1, 141.1, 130.1

(56) References Cited

U.S. PATENT DOCUMENTS

| | | | | |
|---|---|---|---|---|
| 4,400,376 A | * | 8/1983 | Sanderson | 424/88 |
| 4,478,823 A | * | 10/1984 | Sanderson | 424/88 |
| 4,582,865 A | * | 4/1986 | Balazs et al. | 524/29 |
| 4,981,792 A | | 1/1991 | Inamine et al. | 435/119 |
| 5,118,678 A | | 6/1992 | Kao et al. | 514/183 |
| 5,128,326 A | * | 7/1992 | Balazs et al. | 514/54 |
| 5,130,307 A | | 7/1992 | Failli et al. | 514/321 |
| 5,177,203 A | | 1/1993 | Failli et al. | 540/456 |
| 5,202,258 A | | 4/1993 | Chen et al. | 435/252.6 |
| 5,268,370 A | | 12/1993 | Arison et al. | 514/184 |
| 5,270,187 A | | 12/1993 | Chen et al. | 435/118 |
| 5,322,772 A | | 6/1994 | Soldin | 435/7.9 |
| 5,414,135 A | * | 5/1995 | Snow et al. | 568/29 |
| 5,441,977 A | | 8/1995 | Russo et al. | 514/411 |
| 5,504,091 A | | 4/1996 | Molnar-Kimber et al. | 514/291 |
| 5,543,332 A | * | 8/1996 | Lihme et al. | 436/528 |
| 5,604,092 A | | 2/1997 | Erlanger et al. | 435/5 |
| 5,635,406 A | | 6/1997 | Grenier et al. | 436/536 |
| 6,046,170 A | * | 4/2000 | Burhop et al. | 514/21 |
| 6,106,828 A | | 8/2000 | Bisgard-Frantzen et al. | 424/94.1 |
| 6,207,385 B1 | * | 3/2001 | Stanley | 435/6 |
| 6,309,646 B1 | * | 10/2001 | Lees | 424/195.11 |

FOREIGN PATENT DOCUMENTS

| | | | |
|---|---|---|---|
| EP | 0 323 692 | * | 7/1989 |
| SE | 1423316 | * | 2/1976 |
| WO | WO 9301498 | * | 1/1993 |
| WO | WO 93/25533 | | 12/1993 |
| WO | WO 94/24304 | | 10/1994 |
| WO | WO 94/25022 | | 11/1994 |
| WO | WO 94/25072 | | 11/1994 |
| WO | WO 96/18102 | | 6/1996 |

OTHER PUBLICATIONS

Lihme et al. J. Chromatogr. 376:299–305, 1986.*
Porath et al. FEBS Lett. 185: 306–310, 1985.*
Walzel et al. Biomedica Niochemica Acta 50:151–157, 1991.*
Houen et al. J. Immunological Methods 181: 187–200, 1995.*
Somayaji et al. Cancer Biother. Radiopharm. 11:405–414, 1996.*
Ed Harlow et al., "Antibodies A Laboratory Manual", pp. 341 and 324, Cold Spring Harbor Laboratory (1998), Cold Spring Harbor Laboratory Press, New York, USA.
Winkler et al., Therapeutic Drug Monitoring 16:281–286, Jun. 1994.
Metcalfe et al., Transplantation 49:798–802, 1990.
Shan S. Wong, "Chemistry of Protein Conjugation and Cross–Linking," Chapter 4, "Homobifunctional Cross–Linking Reagents," pp. 75–145 (1993), CRC Press Ltd.
Shan S. Wong, "Chemistry of Protein Conjugation and Cross–Linking," Chapter 5, "Heterobifunctional Cross–Linkers," pp. 147–194 (1993), CRC Press Ltd.
R. K. Crossland, et al., "Sulfonate Leaving Groups, Structure and Reactivity, 2,2,2–Trifluoroethanesulfonate," Journal of the American Chemical Society, vol. 93, No. 17, pp. 4217–4219 (1971).

(List continued on next page.)

Primary Examiner—S. Devi
(74) Attorney, Agent, or Firm—Fish & Richardson

(57) ABSTRACT

This invention relates to the production of polyclonal and monoclonal antibodies to specific sites of rapamycin (Sirolimus). The reactivity of these poly and monoclonal antibodies make them particularly useful for immunoassays for therapeutic drug monitoring (TDM). These immunoassays or TDM kits may include polyclonal or monoclonal antibodies to specific sites of rapamycin. These kits may also include various combinations of polyclonal antibodies, polyclonal and monoclonal antibodies or a panel of monoclonal antibodies. Rapamycin conjugate immunogens are prepared for the immunization of a host animal to produce antibodies directed against specific regions of the rapamycin molecule. By determining the specific binding region of particular antibody, immunoassays which are capable of distinguishing between the parent molecule, active metabolites, inactive metabolites and other structurally similar immunosuppressant compounds are developed. The use of divinyl sulfone (DVS) as the linker arm molecule for forming rapamycin-protein conjugate immunogens is described. DVS-linked rapamycin-protein conjugates were found to elicit antibodies with greater specificity to the rapamycin molecule than succinate linked conjugates.

8 Claims, 4 Drawing Sheets

OTHER PUBLICATIONS

J. Milton Harris, et al., "Synthesis and Characterization of Poly(ethylene Glycol) Derivatives," Journal of Polymer Science, Polymer Chemistry Edition, vol. 22, pp. 341–352 (1984).

J. Milton Harris, "Laboratory Synthesis of Polyethylene Glycol Derivatives," JMS–Rev. Macromol. Chem. Phys., C25(3), pp. 325–373 (1985).

Tae H. Ji, et al., "Bifunctional Reagents," *Methods in Enzymology*, vol. 91, pp. 580–609 (1983) Academic Press, Inc.

Gary E. Means, et al., "Chemical Modifications of Proteins: History and Applications," Bioconjugate Chem. 1, pp. 2–12 (1990).

Kurt Nilsson, et al., "Immobilization of Ligands with Organic Sulfonyl Chlorides," *Methods in Enzymology*, vol. 104, pp. 56–96 (1984) Academic Press, Inc.

Kurt Nilsson, et al., "Tresyl Chloride–Activated Supports for Enzyme Immobilization," *Methods in Enzymology*, vol. 135, pp. 65–78 (1987) Academic Press, Inc.

William H. Scouten, et al., "Colored Sulfonyl Chloride as an Activating Agent for Hydroxylic Matrices," *Methods in Enzymology*, vol. 135, pp. 79–84 (1987) Academic Press, Inc.

Abraham, R.T., "Mammalian Target of Rapamycin: Immunosuppressive Drugs Uncover a Novel Pathway of Cytokine Receptor Signaling," *Curr. Opin. Immunol.*, Jun. 1998; 10(3):330–336.

Blazar B.R., Taylor, P. A., Panoskaltsis–Mortari A., Vallera D.A., "Rapamycin Inhibits the Generation of Graft–Versus–Host Disease–and Graft–Versus Leukemia–Causing T Cells by Interfering with the Production of Th1 or Th1 Cytotoxic Cytokines," *J. Immunol.*, Jun. 1, 1998; 160(11):5355–5365.

Brunn, G.J., Fadden, P., Haystead, T.A.J., Lawrence, J. C., Jr., "The Mammalian Target of Rapamycin Phosphorylates Sites Having a (Ser/thr)–pro Motif and Is Activated by Antibodies to a Region near its COOH Terminus," *J. Biol. Chem.*, Dec. 19, 1997;272(51): 32547–32550.

Christians U., Sattler M., Schiebel, H. M., Kruse C., Radeke H.H., Linck A., Sewing K–FR, "Isolation of Two Immunosuppressive Metabolites after in Vitro Metabolism of Rapamycin," *Drug Met and Disp.*, 1992; 20(2)186–191.

Donnelly J. G., Soldin S.J., "Partial Characterization of a 52 kDa CsA/FK506/Rapamycin Binding Protein," *Clin Biochem.*, Oct. 1994; 27(4):367–372.

Hale D.A., Gottschalk R., Fukuzaki T., Wood M.L., Maki, T., Monaco A.P., "Superiority of Sirolimus (Rapamycin) over Cyclosporine in Augmenting Allograft and Xenograft Survival in Mice Treated with Antilymphocyte Serum and Donor–specific Bone Marrow," *Transplantation*, Feb. 15, 1997; 63(3):359–364.

Hale, D.A., Gottschalk R., Maki T., Monaco A. P., "Determination of a Improved Sirolimus (Rapamycin)–based Regimen for Induction of Allograft Tolerance in Mice Treated with Antilymphocyte Serum and Donor–specific Bone Marrow," *Transplantation*, Feb. 27, 1998; 65(4):473–479.

Hashemolhosseini S., Nagamine Y., Morley S. J., Desrivieres S., Mercep L., Ferrari S., "Rapamycin Inhibition of the G1 to S Transition is Mediated by Effects on Cyclin D1 mRNA and Protein Stability," *J. Biol. Chem.*, Jun. 5, 1998; 273(23): 14424–14429.

Kawasone H., Papst P., Webb S., Keller G.M., Johnson G.L., Gelfand E. W., Terada N., "Targeted Disruption of p70(s6k) Defines its Role in Protein Systhesis and Rapamycin Sensitivity," *Proc. Natl. Acad. Sci., U.S.A.*, Apr. 28, 1998; 95(9):5033–5038.

Luengo J.L., Yamashita D.S., Dunnington D., Konialian Beck A., Rozamus L.W., Yen H.K., Bossard M. J., Levy M.A, Hand, A., Newman–Tarr T., Badger A., Faucette L., Johnson R. K., D'Alessio K., Porter T., Shu, A.Y.L., Heys R., Choi J., Kongsaeree P., Clardy J., Holt D.A., "Structure–activity Studies of Rapamycin Analogs: Evidence That the C–7 Methoxy Group is Part of the Effetor Domain and Positioned at the FKBP12–FRAP Interface," *Chem. and Biol.*, Jul. 1995; 2:471–481.

Marigiannis A.P., Hoskin D.W., "Inhibition of CTL Induction by Rapamycin: IL–2 Rescues Granzyme B and Perforin Expression but Only Partially Restores Cytotoxic Activity," *J. Immunol.*, Nov. 15, 1997; 159(10):4700–4707.

Napoli K.L., Kahan B.D., "Routine Clinical Monitoring of Sirolimus (Rapamycin) Whole–blood Concentrations by HPLC with Ultraviolet Detection," *Clin. Chem.*, Dec. 1996; 42(12):1943–1948.

Nickmilder M.J.M., Latinne D., Verbeeck R.K., Janssens W., Svoboda D., Lhoest G.J.J., "Isolation and Identification of New Rapamycin Dihydrodiol Metaoblites from Dexamethasone–induced Rat Liver Microsomes," *Xenobiotica*, 1997, 27(9):869–883.

Schuler W., Sedrani R., Cottens S., Haberlin B., Schulz M., Schuurman H.J., Zenke G., Zerwes H.G., Schreier M.H., "SDZ RAD, a New Rapamycin Derivative: Pharmacological Properties in Vitro and In Vivo," *Transplantation*, Jul. 15, 1997; 64(1):36–42.

Schuurman H., Cottens S., Fuchs S., Joergensen J., Meerloo T., Sedrani R., Tanner M., Zenke G., Schuler W., "SDZ RAD, a New Rapamycin Derivative; Synergism with Cyclosporine," *Transplantation*, Jul. 15, 1997; 64(1):32–35.

Streit F., Christians U., Shiebel H.M., Meyer A., Sewing K.F., "Structural Indentification of Three Metabolites and a Degradation Product of the Macrolide Immunosuppressant Sirolimus (Rapamycin) by Electrospray–MS/MS after Incubation with Human Liver Microsomes," *Met and Disp.*, 1996; 24(11):1272–1278.

Streit, F., Christians U., Shiebel H.M., Napoli K.L., Ernst L., Linck A., Kahan B. D., Sewing K.F., "Sensitive and Specific Quantification of Sirolimus (Rapamycin) and its Metabolities in Blood of Kidney Graft Recipients by HPLC/Electrospray–Mass Spectrometry," *Clin. Chem.* 1996; 42(9):1417–1425.

Suthanthiran M., Morris R.E., Strom T.B., "Immunosuppressants: Cellular and Molecular Mechanisms of Action," *Am J Kidney Dis*, Aug. 1996, 28(2): 159–17.

Svensson J.O., Brattstrom C., Sawe J., "Determination of Rapamycin in Whole Blood by HPLC," *Ther Drug Monit*, Feb. 1997; 19(1):112–116.

Tsunoda S.M., Aweeka F.T., "The Use of Therapeutic Drug Monitoring to Optimise Immunosuppressive Therapy," *Clin Pharmacokinet*, Feb. 1996; 30(2):107–140.

Wang M.E., Tejpal N., Qu X., Yu J., Okamoto M., Stepkowski S.M., Kahan B.D. "Immunosuppressive Effects of FTY720 Alone or in Combination with Cyclosporine And/or Sirolimus," *Transplantation*, Apr. 15, 1998; 65(7):899–905.

Weng Q.P., Kozlowske M., Belhan C., Zhang A., Comb M.J., Avruch J., "Regulation of the p70 S6 Kinase by Phosphorylation in Vivo. Analysis Using Site–specific Anti–phosphopeptide Antibodies," *J Biol Chem*, Jun. 26, 1998; 273(26):16621–16629.

Yatscoff R.W., Aspeslet L.J., Gallant H.L., "Pharmacodynamic Monitoring of Immunosuppressive Drugs," *Clin Chem*, 1998; 44(2):428–432.

Yatscoff R.W., Boeckx R., Holt D.W., Kahan B.D., LeGatt D.F., Shegal S., Soldin S.J., Napoli K., Stilelr C., "Consensus Guideliens for Therapeutic Drug Monitoring of Rapamycin: Report of the Consensus Panel," *Ther Drug Monit*, 1995; 17:676–680.

Copeland K.R., Yatscoff R.W., "The Isolation, Structural Characterization, and Immunosuppressive Activity of Cyclospirin G ($Nva^2$–Cyclosporine) Metabolites," *Ther Drug Monit*, 1991; 13:281–288.

Malcolm A.J., Messner P., Sleytr U.B., Smith R.H., Unger F.M., "Crystalline Bacterial Cell Surface Layers (S–Layers) as Combined Carrier/Adjuvants for Conjugate Vaccines," in *Immobilised Macromolecules: Application Potentials*, Sleytr UB, Messner D. Pum, D, Springer–Verlag, 1993; Chapter 13, pp. 195–207.

Kissinger C.R., Parge H.E., Knighton D.R., Lewis C.T., Pelletler L.A., Tempczyk A., Kalish V.J., Tucker K.D., Showalter R.E., Moomaw E.W., Gastinel L.N., Habuka N., Chen X., Maldonado F., Barker J.E., Bacquet R., Villafranca J.E., "Crystal Structures of Human Calcineurin and the Human FKBP12–FK506–Calcineurin Complex," *Nature*, Dec. 7, 1995; 378, 641–684.

Griffith J.P., Kim J.L., Kim E.E., Sintchak M.D., Thomson J.A., Fitzgibbon M.J., Fleming M.A., Caron P.R., Hsiao K., Navia M.A., "X–Ray Structure of Calcineurin Inhibited by the Immunophilin–Immunosuppressant FKB12–FK506 Complex," *Cell*, Aug. 11, 1995; 82, 507–522.

Itoh S., Navia M.A., "Structure comparison of Native and Mutant Human Recombinant FKBP 12 Complexes with the Immunosuppressant Drug FK506 (Tacrolimus)," *Protein Science*, 1995; 4:2261–2368.

Michnick S.W., Rosen M.K., Wandless T.J., Karplus M., Schreiber S.L., "Solution Structure of FKBP, a Rotamase Enzyme and Receptor for FK506 and Rapamycin," *Science*, May 1991; 252, 836–839.

Van Duyne, G.D., Standaert R.F., Karplus P.A., Schreiber S.L., Clardy J., "Atomic Structure of FKBP–FK506, an Immunophilin–Immunosuppressant Complex," *Science*, May 1991; 252, 839–842.

Wang C.P., Chan K.W., Schiksnis R.A., Scatina J., Sisenwine S.F., "High Performance Liquid Chromatographic Isolation, Spectroscopic Characterization, and Immunosuppressive activities of Two rapamycin Degradation products," *Journal of Liquid Chromatography*, 1994; 17(16), 3383–3392.

Sattler M., Guengerich F.P., Yun C.H., Christians U., Sewing K.F., "Cytochrome P–450 3A Enzymes Are Responsible for Biotransformation of FK506 and Rapamycin in Man and Rat," *Drug Metabolism and Disposition*, 1992; 20, (5) 753–761.

Dias V.C., Yatscoff R.W., "Investigation of Rapamycin Transport and Uptake Across Absorptive Human Intestinal Cell Monolayers," *Clinical Biochemistry*, Feb. 1994; (27) 31–36.

Sattler M., Geungerich F.P., Christians U., Sewing K.F., "Cytochrome P–450IIIA4 is Involved in Biotransformation of FK506 and Rapamycin in Rat and Human Liver," *Gastroenterology*, 102, (4) Part 2, A880.

* cited by examiner

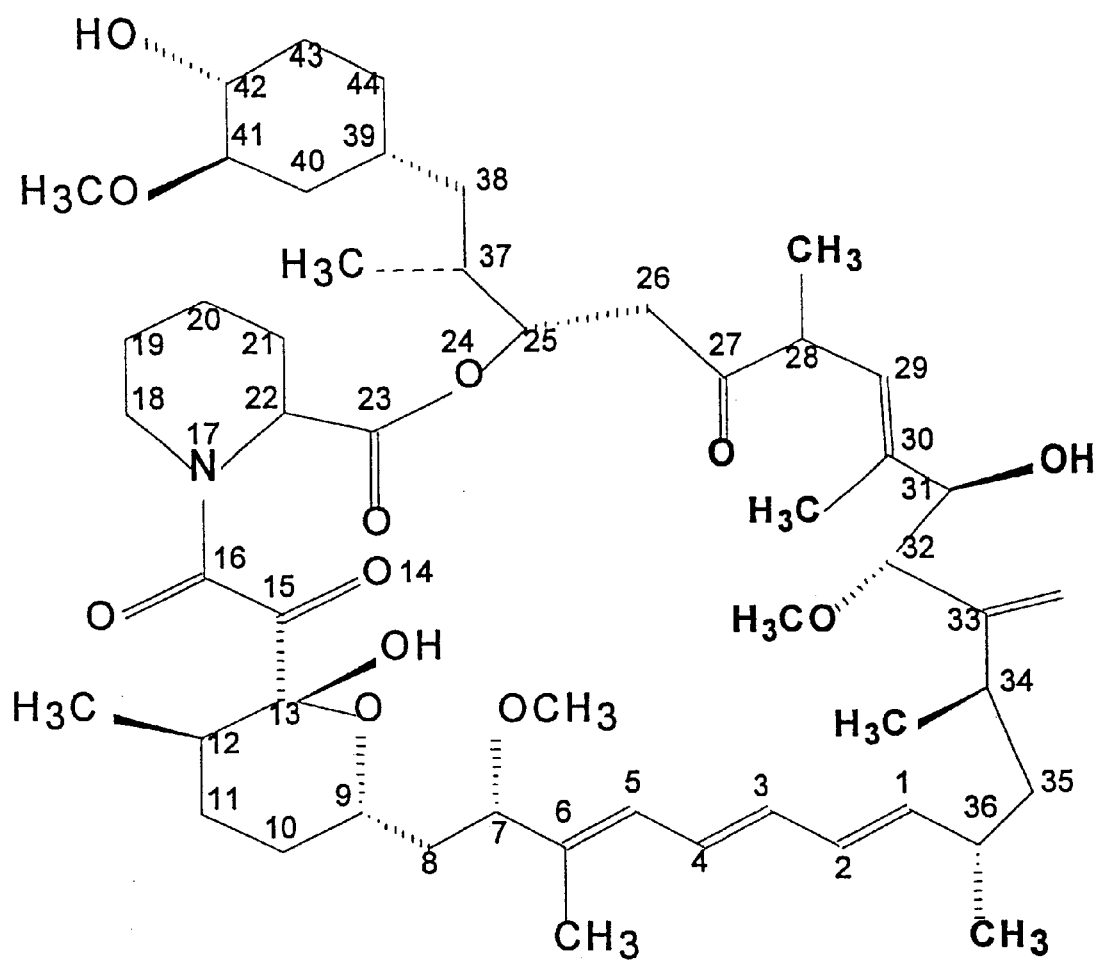
Figure 1: Structure of Sirolimus (RAPA)

Figure 2: Titration Curves of MoAbs to the Rapa-42-KLH Immunogen
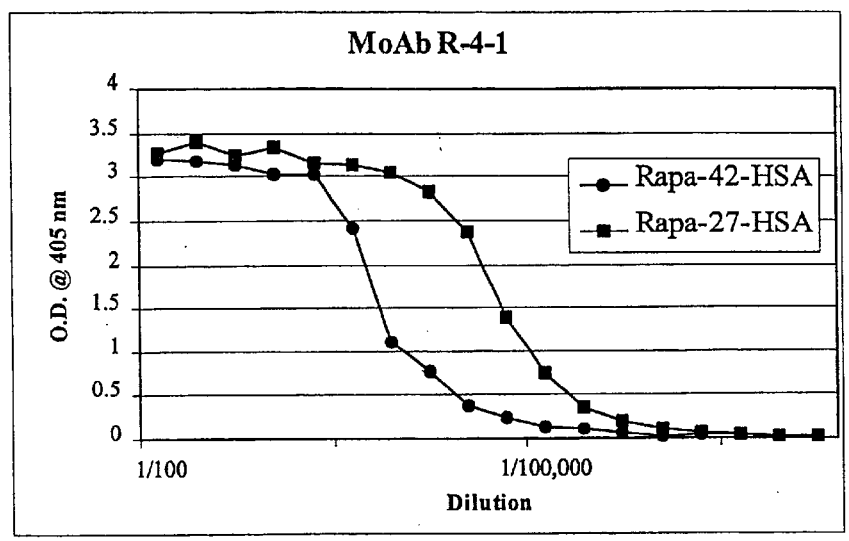
2A
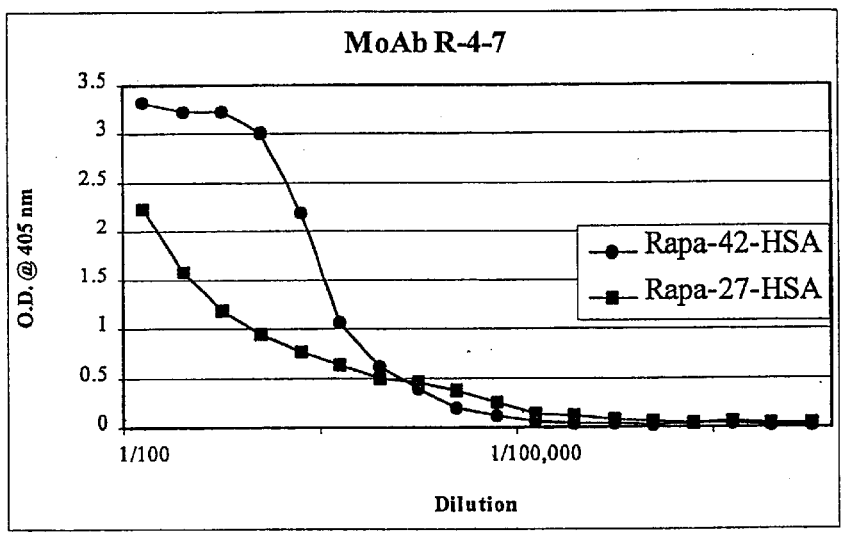
2B
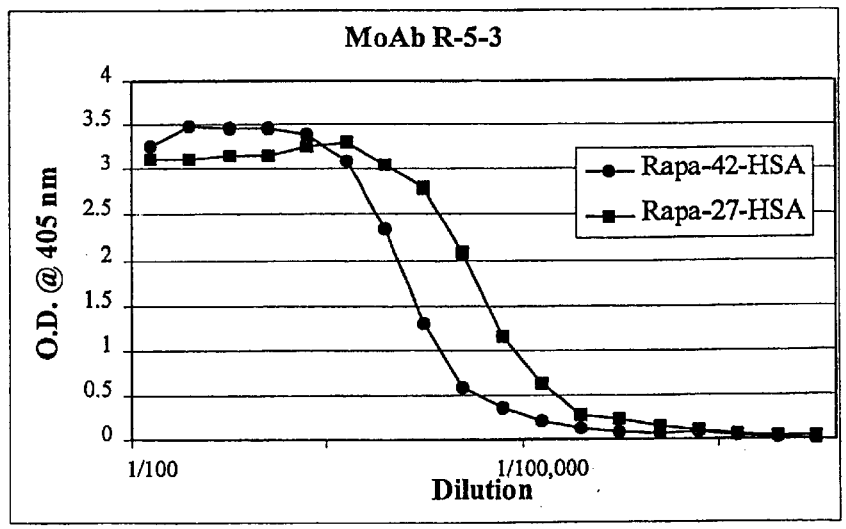
2C Figure 3: Inhibition of R-4-1 and R-5-3 MoAbs by Rapa and RAD
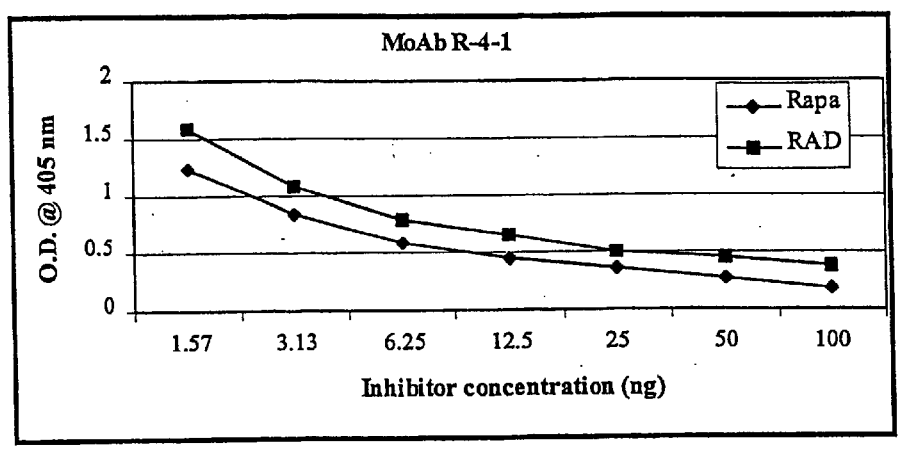
3A
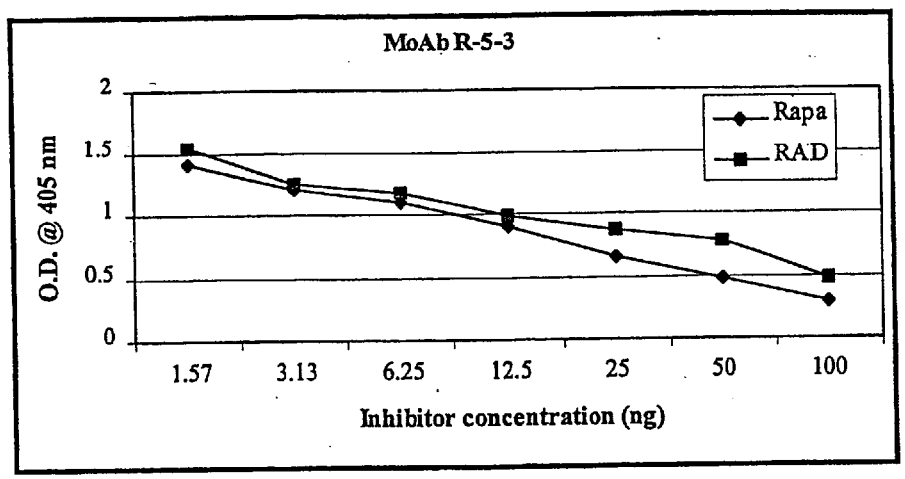
3B Figure 4: Percent Inhibition of MoAb R-5-3
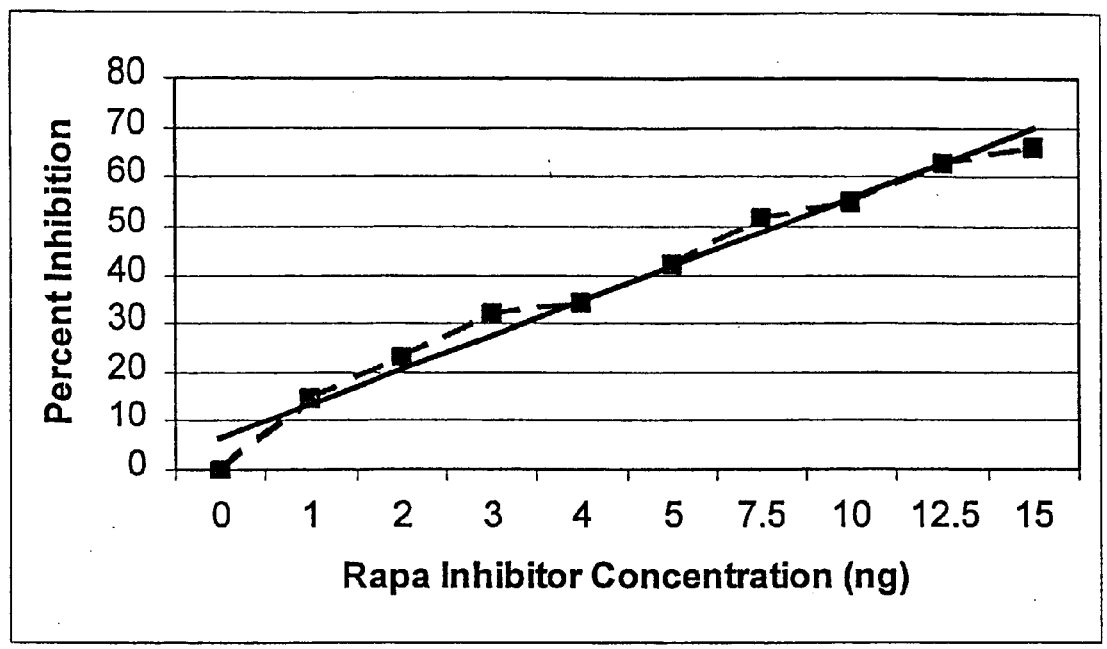

US 6,709,873 B1

METHOD FOR PRODUCTION OF ANTIBODIES TO SPECIFIC SITES OF RAPAMYCIN

This application is a divisional application of U.S. patent application Ser. No. 09/419,877, filed Oct. 15, 1999, now co-pending, which application is a continuation-in-part of U.S. patent application Ser. No. 09/325,994 filed Jun. 4, 1999, now abandoned, which application is a continuation of U.S. patent application Ser. No. 09/101,309 filed Jul. 7, 1998, now abandoned, which application was filed as international patent application PCT/CA98/00361 on Apr. 9, 1998 which claims priority to U.S. provisional patent application No. 60/043,215 filed Apr. 9, 1997. The disclosure of each of the above-referenced applications is incorporated herein by reference in its entirety.

FIELD OF THE INVENTION

This invention relates to the production of polyclonal and monoclonal antibodies to specific sites of rapamycin and/or rapamycin metabolites, derivatives and analogues. The reactivity of these polyclonal and monoclonal antibodies makes them particularly useful for immunoassays for therapeutic drug monitoring (TDM). These immunoassays or TDM kits may include polyclonal or monoclonal antibodies to specific sites of Rapamycin (Rapa) and/or metabolites, derivatives and analogues of rapamycin. These kits may also include various combinations of polyclonal antibodies, polyclonal and monoclonal antibodies or a panel of monoclonal antibodies.

INTRODUCTION AND BACKGROUND

This invention relates to the production of polyclonal and monoclonal antibodies to specific sites of rapamycin (Sirolimus). The reactivity of these poly and monoclonal antibodies make them particularly useful for immunoassays for therapeutic drug monitoring (TDM). These immunoassays or TDM kits may include polyclonal or monoclonal antibodies to specific sites of rapamycin. These kits may also include various combinations of polyclonal antibodies, polyclonal and monoclonal antibodies or a panel of monoclonal antibodies.

Rapamycin (Rapa) is a macrocyclic antibiotic (macrolide lactone), which was originally isolated in soil samples from Easter Island from a *Streptomyces hygroscopicus* strain[1]. Rapamycin is structurally related to the immunosuppressant FK-506 (Tacrolimus) but mechanistically different. Rapamycin has anti-candidal, anti-proliferative and anti-tumor activity. Rapamycin also dampens autoimmune reactions (SLE, adjuvant arthritis, allergic encephalomyelitis). Rapamycin is also a potent immunosuppressant that inhibits T and B cell activation by blocking cytokine-mediated events, and inhibits growth factor mediated cell proliferation. The structure of rapamycin is given in FIG. 1.

Currently, the two most commonly administered immunosuppressive drugs to prevent organ rejection in transplant patients are Cyclosporine (CSA) and FK-506 (FK). Therapeutic monitoring of concentrations of these drugs in blood is required to optimize dosing regimes to ensure maximal immunosuppression with minimal toxicity. Recent clinical data indicates that Rapamycin will be a widely used immunosuppressant to prevent organ rejection in transplant patients. Specific TDM monitoring kits for Rapamycin will therefore be required. The polyclonal and monoclonal antibodies to specific sites of Rapamycin of this invention are ideally suited for developing Rapamycin TDM kits.

Cytochrome $P_{450}3A4$ enzyme metabolizes rapamycin to a number of demethylated and hydroxylated metabolites. The exact pathways of rapamycin metabolism in humans have not been completely elucidated since only a few of the metabolites have been structurally identified. Therefore, no consensus has been established concerning the identity or steady state concentrations in whole blood after oral administration. A summary of the current reported knowledge of rapamycin metabolism follows.

Streit et. al. structurally identified four rapamycin metabolites from rabbit liver microsomes[2]. These include 41-demethyl rapamycin, 7-demethyl rapamycin, 11-hydroxy rapamycin, and a 24-hydroxy ester hydrolysis degradation product of rapamycin. It has also been shown that the metabolites of rapamycin can undergo this ester hydrolysis. Streit also partially identified di, tri, and tetra hydroxylated rapamycin metabolites. Wang et. al. found 16 hydroxylated and/or demethylated metabolites in the bile of rapamycin treated rats[3]. Nickmilder et. al. identified a 3,4 and 5,6 dihydrodiol rapamycin metabolite in rat liver microsomes.[4] In trough whole blood, Streit et. al. have identified 41-demethyl, dihydroxy, and didemethyl rapamycin metabolites.[5] These metabolites accounted for 56% of total rapamycin derivatives measured. Finally, Leung et. al. looked at the disposition of $[^{14}C]$-rapamycin in healthy male volunteers.[6] They found that rapamycin represented approximately 35% of the total radioactivity in blood and that 41-demethyl, 7-demethyl, and several hydroxy, hydroxydemethyl, and didemethyl rapamycin metabolites individually represented between 1 and 12% of the total radioactivity. They also found there was no notable presence of glucuronide or sulfate conjugates in blood, feces, or urine and that most of an oral dose was eliminated in feces. Rapamycin metabolites can be isolated from a number of various sources, including but not limited to blood, urine or feces samples, from liver microsomes or from microorganism cultures.

There is a need for improved methods of monitoring levels of rapamycin and/or rapamycin metabolites and derivatives.

SUMMARY OF THE INVENTION

The current invention is drawn to methods for the preparation of immunogenic conjugates which elicit antibodies with specificity for rapamycin related compounds. For the purposes of this application, the term rapamycin related compound is meant to include any or all of the rapamycin molecule itself and/or various rapamycin metabolites and derivatives. Rapamycin and rapamycin metabolite and/or derivative conjugate immunogens are prepared and used for the immunization of a host animal to produce antibodies directed against specific regions of the rapamycin or metabolite and/or derivative molecules. By determining the specific binding region of a particular antibody, immunoassays which are capable of distinguishing between the parent molecule, active metabolites, inactive metabolites and other rapamycin derivatives/analogues are developed. The use of divinyl sulfone (DVS) as the linker arm molecule for forming rapamycin/metabolite/derivative-protein conjugate immunogen is described.

In a first aspect, the invention provides antibodies which are capable of binding to a rapamycin related compound. Such antibodies which recognize a specific region of said rapamycin related compound, the Rapa derivative RAD or the Rapa metabolites M1 to M5 are preferred. Monoclonal antibodies (MoAbs) are most preferred. Also provided are methods for producing an antibody which is capable of recognizing a specific region of rapamycin related compound, said methods comprising: a) administering an immunogen comprising a rapamycin related compound, a linker arm molecule and a protein carrier to an animal so as to effect a specific immunogenic response to the rapamycin related compound; b) recovering an antibody to said rapamycin related compound from said animal; and c) identifying the antibody binding region by measuring the reactivity of the antibody to at least one rapamycin related compound. Such methods wherein said linker arm molecule is divinyl sulfone and where the rapamycin related compound is linked to the carrier at the 27, 31, 41 or 42 position are preferred. The protein carrier may preferably be keyhole limpet hemocyanin or human serum albumin. Use of hybridoma cells to accomplish the above methods is also provided.

In another aspect, the invention provides immunoassay methods for measuring the level of a rapamycin related compound in a mammal, comprising: a) incubating a biological sample from said mammal with at least one antibody which is capable of binding to a rapamycin related compound; and b) measuring the binding of rapamycin related compound to said antibody. Use of antibodies which recognize a specific region of said rapamycin related compound, the Rapa derivative RAD or the Rapa metabolites M1 to M5 in these assays is preferred. Use of monoclonal antibodies is most preferred. Immunoassay kits for measuring the level of a rapamycin related compound in a sample, said kits comprising an antibody as described above are also provided.

BRIEF DESCRIPTION OF THE DRAWING FIGURES

FIG. 1 shows the structure of Rapamycin (Sirolimus).

FIGS. 2A–2C illustrate titration curves of several monoclonal antibodies (MoAbs) to the rapamycin immunogen Rapa-42-KLH.

FIG. 3A–3B illustrate the inhibition of MoAbs R-4-1 and R-5-3 by rapamycin and a 42-0-(2-hydroxy-ethyl) derivative of rapamycin (RAD).

FIG. 4 illustrates the inhibition of MoAb R-5-3 by a 0–15 ng range of rapamycin.

DETAILED DESCRIPTION OF THE INVENTION

Rapamycin conjugate immunogens are prepared for the immunization of a host animal to produce antibodies directed against specific regions of the rapamycin molecule. By determining the specific binding region of particular antibody, immunoassays which are capable of distinguishing between the parent molecule, active metabolites, inactive metabolites and other structurally similar immunosuppressant compounds are developed. The use of divinyl sulfone (DVS) as the linker arm molecule for forming rapamycin-protein conjugate immunogens is described. DVS-linked rapamycin-protein conjugates were found to elicit antibodies with greater specificity to the rapamycin molecule than succinate linked conjugates.

The following examples describe the best mode for carrying out the invention. The examples describe isolation Rapa metabolites, preparation of haptens, immunization of animals to elicit antibody responses, characterization of antibody reactivity, production and selection of polyclonal and monoclonal antibodies to Rapa and Rapa metabolites or derivatives and assays using the antibodies provided by the present invention.

The following Examples are not intended to limit the scope of the invention in any manner.

EXAMPLE 1

Synthesis of Rapamycin-42-Divinyl Sulfone and Conjugation to a Protein Carrier

Preparation of rapamycin-42 divinyl sulfone hapten: Rapamycin (0.5 mmol) (Calbiochem-Novabiochem, San Diego, Cat.# 553210) was dissolved in dichloromethane and treated with 10 equivalents of 2-t-Boc aminoethylchloroimidate and the reaction mixture is cooled to 0 C. To this solution, 4 mL of trimethylsilyl triflate was added in one addition. The reaction mixture was stirred at 0° C. for 24 hours. Then the reaction mixture was diluted with dichloromethane (100 mL and washed with water (50 mL×3)). The organic solution was dried and concentrated and the mixture subjected to column chromatography to remove the excess of chloroimidate reagent. This material was analyzed-using MS-flow injection electrospray mass spectrometry. The derivatized rapamycin was then treated with trifluoroacetic acid to remove the amino protecting group. The reaction mixture was then diluted with dichloroqiethane (50 mL) and washed in warm water. The organic solution was dried and concentrated to get the aminoethyl derivative of rapamycin. Without further purification, the reaction mixture was treated with an excess of divinylsulfone in dichloromethane solution using anhydrous potassium carbonate as the catalyst. The reaction mixture was stirred for 24 hours and then diluted with dichloromethane and washed with water to remove the carbonate. The organic solution was dried and concentrated and the crude project subjected to column chromatography to remove the excess of divinyl sulfone. The isolated product was used for conjugation without further purification.

Preparation of rapamycin-42 divinyl sulfone conjugate: Conjugation of the rapamycin-42-divinyl sulfone derivative was performed by preparing a solution of the rapamycin-42-divinyl sulfone derivative in dimethyl sulfoxide which was then slowly added to a rapidly stirred solution of keyhole limpet hemocyanin (KLH) or human serum albumin (HSA) in 0.2M phosphate buffer (pH 7.6). Stirring of the mixture was continued at room temperature for 24 hours followed by isolation of the rapamycin-42-divinyl sulfone protein conjugate by dialysis.

EXAMPLE 2

Synthesis of Rapamycin-42-Succinate and Conjugation to a Protein Carrier

Preparation of rapamycin-42-O-hemisuccinate: Dimethylaminopyridine (11.8 mg, 97 μmol) was added to a solution of rapamycin (80.0 mg, 88 μmol) and succine anhydride (30.7 mg, 307 μmol) in 2 mL dry pyridine and the mixture stirred at room temperature for 23 hours. The pyridine was evaporated and the residue dissolved in ethyl acetate. The ethyl acetate solution was washed twice with water and finally with brine before drying over magnesium sulfate and evaporating the solvent. The residue was eluted through a silica gel column using methanol/chloroform (1:19) and then methanol/chloroform (1:9) as eluent to give 20.0 mg (23%) of the product as a colorless solid.

Preparation of 42-O-succinimidooxysuccinyl rapamycin: N-hydroxysuccinimide (2.3 mg 19.7 μmol) was added to a solution of rapamycin-42-O-hemisuccinate (20.0 mg, 19.7 μmol) and 1-ethyl-3-(3-dimethylaminopropyl) carbodiimide (EDAC) (3.8 mg, 19.7 μmol) in 5 mL of dry dichloromethane and the mixture stirred overnight at room temperature. The solvent was evaporated and the residue eluted through a silica gel column using ethyl acetate as eluent to give 5.7 mg (26%) of the product as a colorless solid.

Analysis of rapamycin-42-O-hemisuccinate and 42-O-succinim-idooxysuccinyl rapamycin: Purified rapamycin-42-O-hemisuccinate (1013.5 daltons) was identified as the sodium adduct (1036.5 daltons) by electrospray ionization mass spectrometry and structurally characterized by fragmentation in the negative-ion mode. Purified 42-O-succinimidooxysuccinyl rapamycin (1110.5 daltons) was identified as the sodium adduct (1133.5 daltons) by electrospray ionization mass spectrometry.

Preparation of rapamycin-42-O-succinate conjugates: A solution of 42-O-succinimidooxysuccinyl rapamycin (2.0 mg) in 500 mL of dimethyl sulfoxide was slowly added into a rapidly stirred solution of keyhole limpet hemocyanin (KLH) (3.0 mg) or human serum albumin (HSA) in 2 mL of 0.1 M aqueous sodium bicarbonate adjusted to pH 7.7 with acetic acid. Stirring of the mixture was continued at room temperature for 24 hours followed by isolation of the rapamycin-42-divinyl sulfone protein conjugate by dialysis.

EXAMPLE 3

Synthesis of Rapamycin-27-Oxime-Divinyl Sulfone and Conjugation to a Protein Carrier Preparation of rapamycin-27-oxime: Hydroxylamine hydrochloride (3.0 mg, 44 μmol) in 100 mL of water was added to a solution of rapamycin (20.0 mg, 22 μmol) and pyridine (40 mL) in 4 mL of ethanol and the reaction mixture stirred at room temperature for 24 hours. The reaction mixture was diluted with ethyl acetate and washed sequentially with water, dilute aqueous hydrochloric acid, and brine. The organic phase was dried over magnesium sulfate and the solvent evaporated to give 20 mg of crude product.

Analysis of rapamycin-27-oxime-divinyl: LC/MS analysis (Gradient condition: 25/25/50 water/acetonitrile/methanol at 0 minutes up to 20/30/50 water/acetonitrile/methanol at 18 minutes. Column: SPHERISORB™ C-8 (octyl bonded spherical silica packing, Waters) semi-prep. Temperature was 35° C. and the flow rate set at 3.5 mL/min. The UV signal was monitored at 276 nm) of the crude residue indicated that there were two isomeric forms of the oxime as well as a small amount of unreacted rapamycin. Negative-ion fragmentation of Rapa-Oxime is consistent with oxime formation at C-27. The mixture was used without purification for further reaction.

Preparation of the rapamycin-27-oxime-divinyl sulfone hapten (Rapa-Ox-DVS): Vinyl sulfone (203 mg ,1.72 μmol) was added to a mixture of the crude rapamycin-27-oxime (20 mg, 22 μmol) and dried anhydrous potassium carbonate (80 mg) in 10 mL dry dichloromethane at room temperature and under a nitrogen atmosphere. The mixture was stirred for 17 hours. Passing a stream of nitrogen through the flask evaporated the solvent and the resulting residue was immediately quenched with 10 mL of a solution of 10 drops acetic acid in 10 mL methanol. The clear solution was then decanted off from the remaining potassium carbonate granules and the solution concentrated. The residue was passed through a silica gel column using a gradient of methanol/chloroform (1% to 5% methanol) as eluent to separate the reaction products from excess vinyl sulfone.

Analysis of rapamycin-27-oxime-divinyl-sulfone hapten (Rapa-Ox-DVS): The crude reaction residue was resolved by reversed-phase HPLC (Gradient condition: 40/10/50 water/acetonitrile/methanol from 0 to 5 minutes, up to 25/25/50 water/acetonitrile/methanol from 5 to 40 minutes, followed by 50/50 acetonitrile/water from 40 to 45 minutes. Column: SPHERISORB™ C-8 (octyl bonded spherical silica packing, Waters) semi-prep. Temperature was 35° C. and the flow rate set at 3.5 mL/min. The UV signal was monitored at 276 nm) into 3 major rapamycin-Ox-DVS species; Rapa-Ox-DVS (species X) Rapa-Ox-DVS (species 2); Rapa-Ox-DVS (species 3) which were identified by electrospray ionization mass spectrometry. Under the gradient conditions specified both Rapa-Ox-DVS (species X) and Rapa-Ox-DVS (species 2) elute as pure product while Rapa-Ox-DVS (species 3) was further purified using a 35/15/50 water/acetonitrile/methanol isocyanic mixture and identical chromatographic conditions as above.

The positive-ion fragmentation pattern for Rapa-Ox-DVS (species 2) is consistent with rapamycin modification through the C-27 position. The LC/MS profile and mass spectrum was obtained for purified Rapa-Ox-DVS (species 3). The positive-ion fragmentation pattern for Rapa-Ox-DVS (species 3) was again consistent with rapamycin modification through the C-27 position. The yields for each species were as follows:

Rapa-Ox-DVS-(X): 2.4 mg (10%)
Rapa-Ox-DVS-(2): 3.4 mg (15%)
Rapa-Ox-DVS-(3): 0.5 mg (2%)

Preparation of rapamycin-oxime-Divinyl Sulfone Conjugates: A solution of Rapa-Ox-DVS (species 2) (0.3 mg) in 300 mL of dimethyl sulfoxide was slowly added into a rapidly stirred solution of keyhole limpet hemocyanin (KLH) (1.0 mg) in 1 mL of 0.2M phosphate buffer (pH 7.6) and the mixture stirred at room temperature for 24 hours. The reaction mixture was then dialyzed to recover the rapamycin-oxime-divinyl sulfone protein conjugate. A Rapa-Ox-DVS (species 2)-HSA conjugate was prepared in the same manner.

EXAMPLE 4

Synthesis of Rapamycin-31-Divinyl Sulfone and Conjugation to a Protein Carrier

Preparation of a rapamycin-31-divinyl sulfone hapten (Rapa-DVS): Vinyl sulfone (82.6 mg, 0.7 μmol) was added to a mixture of rapamycin (5.0 mg, 5.5 μmol) and dried anhydrous potassium carbonate (30 mg) in 3 mL of dry acetone at room temperature under a nitrogen atmosphere. The mixture was stirred for 19 hours. Passing a stream of nitrogen through the flask evaporated the solvent and the resulting residue was immediately quenched with 5 mL of a solution of 10 drops of acetic acid in 10 mL methanol. The clear solution was then decanted off the potassium carbonate granules and the solution concentrated. The residue was passed through a silica gel column using a gradient of methanol/chloroform (1% to 2% methanol) as eluent to separate the reaction products from excess vinyl sulfone. The combined reaction products were then purified and analyzed as follows.

Analysis of a rapamycin-31-divinyl sulfone hapten (Rapa-DVS): The crude reaction residue was analyzed by LC/MS (Gradient condition: 25/25/50 water/acetonitrile/methanol at 0 minutes up to 20/30/50 water/acetonitrile/methanol at 18 minutes. Column: SPHERISORBI C-8 (octyl bonded spherical silica packing, Waters) semi-prep. Temperature was 35° C. and the flow rate set at 3.5 mL/min. The UV signal was monitored at 276 nm and found to contain 1 major species of Rapa-DVS along with its isomer. Rapa-DVS was purified using an isocyanic mobile phase of 40/10/50 water/acetonitrile/methanol (containing 10% Tert-butyl methyl ether) and identical chromatographic conditions as above. The LC/MS profile and mass spectrum of purified Rapa-DVS was obtained. The positive-ion fragmentation pattern for Rapa-DVS is consistent with rapamycin modification through the 31-OH position. The obtained yield was 0.1 mg (2%).

Preparation of rapamycin-31-divinylsulfone conjugates: Rapa-31-DVS-KLH and HSA conjugates were prepared as described in Example 3.

EXAMPLE 5

Isolation and Characterization of Rapamycin Metabolites

Biosynthesis of Rapamycin Metabolites Utilizing Rabbit Liver Microsomes:

The basic procedure utilized for isolating rapamycin metabolites was as follows: 1. Preparation of Rabbit Liver Microsomes A fresh or frozen rabbit liver (not induced) was washed with approximately 750 mL of 1.15% KCl (w/v) and cut into small pieces (approximately 5 mm$^3$). These were placed into a small conical 50 mL centrifuge tube with 15 mL of 1.15% KCl and stored on ice. After the whole liver was processed, the pieces were homogenized using a Beckman Polytron™ homogenizer into a microsomal suspension that was centrifuged at 10,000×g for 20 min. Following centrifugation the supernatant was decanted into specialized centrifuge tubes and placed on ice. These were centrifuged again, using an ultracentrifuge, for 60 min at 100,000×g. This process yielded a microsomal pellet which contains the cytochrome $P_{450}$ enzymes required for the metabolism of rapamycin. The microsomes were then re-suspended in 1.15% KCl, tested for protein concentration using the Lowry method, and stored at −70° C.

2. Biosynthesis of Rapamycin Metabolites

Incubation mixtures have a final volume of 45 mL, and contained 22.5 mg of rapamycin dissolved in 1.8 mL DMSO. The reaction mixture also contained 0.1 M sodium phosphate buffer (pH 7.4), 0.5 mM EDTA, 5.0 mM MgCl$_2$, 3.5 mM NADPH, 1.5 mM NADP, 50 mM glucose-6-phosphate, 10 units per mL of glucose-6-phosphate dehydrogenase, and 10 mg/mL of microsomal protein.

The biotransformation reaction was carried out in 250 mL Erlenmeyer flasks. The microsomal solution, without drug, was allowed to incubate at 37° C. for 5 min in an environmentally controlled incubator shaker. The reaction was initiated by adding the drug and allowing the reaction to proceed for two hours. At this time, the reaction was stopped by removing the flasks from the incubator, transferring their contents into 50 mL centrifuge tubes, and storing them at −20° C.

3. Metabolite Isolation

The metabolites were isolated by thawing the stored reaction mixtures and transferring them to 500 mL glass bottles (100 mL of reaction mixture per bottle). This solution was acidified with an equal volume of 0.2 M acetic acid (pH 3.0) and extracted two times with 200 mL MTBE (methyltert- butyl ether). The solvent was recovered and evaporated to dryness using a rotary evaporator. The residue was reconstituted in methanol and stored at −70° C.

4. Metabolite Purification

A Waters chromatographic system comprised of a 600E gradient controller plus pump, 717 autosampler, 486 UV detector, and Millenium workstation was used to separate and purify the rapamycin metabolites. The column utilized for initial separation was a Waters C8 reverse phase (10×250 mm) SPHERISORB™ C-8 (octyl bonded spherical silica packing, Waters) semi-prep HPLC column. The metabolites were separated using a column temperature of 60° C. and a flow of 2.5 mL/min. The initial mobile phase consisted of 40% water and 60% methanol. To achieve the best separation, this composition was programmed to change over 50 min as indicated in the following table:

| Time (min) | Flow (mL/min) | Water (%) | Acetonitrile (%) | Methanol (%) | Comment |
|---|---|---|---|---|---|
| 0.00 | 2.5 | 40 | 0 | 60 | Gradient |
| 40.00 | 2.5 | 20 | 60 | 20 | |
| 40.01 | 2.5 | 20 | 40 | 40 | Wash |
| 50.00 | 2.5 | 40 | 0 | 60 | Equilibrate |

Individual peaks were collected, pooled, and labeled. Each of these peaks represents a rapamycin metabolite(s). Using the same chromatographic system, the peaks collected were subjected to further purification using a Waters C18 (octadecyl bonded spherical silica packing) reverse phase (3.6×150 mm) Symmetry column. The column temperature utilized was 60° C., the flow was 1.0 mL/min, and the mobile phase consisted of a water/methanol gradient that was specific for each metabolite purified.

| Rapamycin Metabolite Species Identified from Microsome Preparations: | | | |
|---|---|---|---|
| Molecular Adduct Mass | Species | Peak Designation | Metabolite Designation |
| 922 | 7-O-Demethyl Rapa | D4 | M3 |
| 922 | 41-O-Demethyl Rapa | F1 | M4 |
| 922 | 32-O-Demethyl Rapa | | |
| 908 | 32,41-Demethyl Rapa | C5 | M5 |
| 908 | Didemethyl Rapa | | |
| 952 | C9-C23 Hydroxy Rapa | D1 | M1 |
| 952 | C1–C8 or C32–C36 Hydroxy Rapa | D3 | M2 |
| 952 | Hydroxy Rapa | | |
| 938 | 41-O-Demethyl, C1–C8 or C32–C36 Hydroxy Rapa | C1 | |
| 894 | 7,32,41 Tridemethyl Rapa | | |
| 954 | demethyl, Dihydroxy Rapa or Ester Hydrolysis | A8 | |
| 970 | demethyl, Trihydroxy Rapa or Dihydrodiol Rapa | A3 + A4 | |
| 968 | Dihydroxy Rapa | B or C | |

EXAMPLE 6

Immunization to Elicit Rapamycin Specific Antibody Responses

The basic immunization protocols are as follows:

Typically, mice are immunized on day 0 (1°—primary immunization), day 7 (2°—secondary immunization), and day 28 (3°—tertiary immunization) by subcutaneous or intraperitoneal injection with rapamycin—conjugate immunogens at doses of 5, 10, 15, or 20 μg based on protein content. Mice were bled 7–10 days post 2° and 3° immunization to collect serum to assay antibody responses. Various other immunization schedules are effective, including day 0 (1°), day 7 (2°) and days 14, 21 or 30 (3°); day 0 (1°), day 14 (2°), and days 28 or 44 (3°); and day 0 (1°), day 30 (2°) and day 60 (3°). Thirty days post-tertiary immunization a booster may be injected, subsequent monthly boosters may be administered.

Immunized mice are I.V. or I.P. injected with immunogen in PBS as a final boost 3–5 days before the fusion procedure. This increases the sensitization and number of immunogen specific B-lymphocytes in the spleen (or lymph node tissues). This final boost is administered 2 to 3 weeks after the previous injection to allow circulating antibody levels to drop off.

Such immunization schedules are useful to immunize mice with rapamycin immunogen conjugates to elicit specific polyclonal antiserum and for the preparation of specific monoclonal antibodies. The immunogen compositions are also useful for immunizing any animal capable of eliciting rapamycin specific antibodies, such as bovine, ovine, caprine, equine, leporine, porcine, canine, feline, avian and simian species. Both domestic and wild animals may be immunized. The route of administration may be any convenient route, and may vary depending on the animal to be immunized, and other factors. Parental administration, such as subcutaneous, intramuscular, intraperitoneal or intravenous administration, is preferred. Oral or nasal administration may also be used, including oral dosage forms, which are enteric coated.

Exact formulation of the compositions will depend on the species to be immunized and the route of administration. The immunogens of the invention can be injected in solutions such as 0.9% NaCl (w/v), PBS or tissue culture media or in various adjuvant formulations. Such adjuvants could include, but are not limited to, Freund's complete adjuvant, Freund's incomplete adjuvant, aluminum hydroxide, dimethyldioctadecylammonium bromide, Adjuvax™ (Alpha-Beta Technology), Imject Alum™ (Pierce), Monophosphoryl Lipid A (Ribi Immunochem Research), Titermax™ (CytRx), toxins, toxoids, glycoproteins, lipids, glycolipids, bacterial cell walls, subunits (bacterial or viral), carbohydrate moieties (mono-, di-, tri-, tetra-, oligo- and polysaccharide), dextran sulfate, various liposome formulations or saponins.

Combinations of various adjuvants may be used with the immunogen conjugates of the invention to prepare a pharmaceutical composition.

The conjugates of this invention may be used as immunogens to elicit rapamycin or rapamycin metabolite specific polyclonal antibody, and to stimulate B-cells for specific monoclonal antibody production. They may also be utilized as development and/or research tools, as diagnostic reagents in immunoassay kit development, as prophylactic agents (for example, to block cell receptors) and as therapeutic modalities as immunomodulators and as drug delivery compositions.

EXAMPLE 7

Assays to Determine Antibody Reactivity to Rapamycin Immunogens

The basic direct ELISA protocol for determining antibody reactivity to rapamycin used in the invention was as follows:

Direct ELISA Protocol

1. Use Falcon Pro-bind immunoplate.
2. Dilute coating antigen to 1.0 μg/mL in carbonate-bicarbonate buffer.
 Use glass tubes.
3. Add 100 μL to each well of plate. Store overnight at 4° C.
4. Shake out wells and wash 3× with 200 μL PBS/0.05% TWEEN™ (polyoxyethylene-sorbitol) (v/v) per well.
5. Add blocking buffer, 100 μL per well (PBS/2% BSA (w/v)).
 Incubate for 60 min at 37° C.
6. Wash 3× as in step 4.
7. Add 100 μL per well of test antibody appropriately diluted in PBS/0.1% TWEEN™ (polyoxyethylene-sorbitol) (v/v). Incubate 60 min at 37° C.
8. Wash 3× as in step 4.
9. Dilute alkaline phosphatase conjugated anti-mouse IgG (Tago cat # AMI 4405) in PBS/0.1% TWEEN™ (polyoxyethylene-sorbitol) (v/v) to 1:2000 concentration. Add 100 μL per well and incubate at 37° C. for 60 min.
10. Wash 3× as in step 4.
11. Prepare enzyme substrate using Sigma #104 alkaline phosphatase substrate tablets (1 mg/mL in 10% diethanolamine (v/v) substrate buffer). Add 100 μL per well and incubate in the dark at room temperature. Absorbance can be read at 405 nm at approximately 15-min intervals.

To measure antibody isotype levels (IgM, IgG and IgA isotypes) elicited to rapamycin immunogens the following basic procedure was used:

Isotyping ELISA Protocol

1. Use Falcon® Pro-bind™ immunoplates.
2. Dilute coating antigen to 1 μg/mL in carbonate-bicarbonate buffer. Add 100 μL per well and incubate overnight at 4° C.
3. Shake out wells and wash 3× with 200 μL PBS/0.05% TWEEN™ (polyoxyethylene-sorbitol) (v/v) per well.
4. Add 200 μL blocking buffer per well (PBS/2% BSA (w/v)).
 Incubate 60 min at room temperature.
5. Wash as in step 3.
6. Add 100 μL per well of tissue culture supernatant undiluted or mouse serum diluted to 1/100 in PBS/0.1% TWEEN™ (polyoxyethylene-sorbitol) (v/v). Incubate for 60 min at 37° C.
7. Wash as in step 3.
8. Prepare 1:2 dilution of EIA grade mouse type (rabbit anti-mouse IgM, IgG1, IgG2a, IgG2b, IgG3 and IgA, Bio-Rad) in dilution buffer (PBS/0.1% Tween (v/v)). Add 100 μL per well into appropriate wells and incubate 60 min at 37° C.
9. Wash as in step 3.
10. Dilute alkaline phosphatase conjugated anti-rabbit IgG (Tago cat # 4620) in PBS/0.1% TWEEN™ (polyoxyethylene-sorbitol) (v/v) to 1:2000 concentration. Add 100 μL per well and incubate at 37° C. for 60 min.
11. Wash as in step 3.
12. Prepare enzyme substrate using Sigma # 104 alkaline phosphatase substrate tablets (1 mg/mL in 10% diethanolamine (v/v) substrate buffer). Add 100 μL per well and incubate in the dark at room temperature. Absorbance can be read at 405 nm at approximately 15-min intervals.
13. Absorbance readings may be converted to μg antibody per ml serum using dose-response curves generated from ELISA responses of the rabbit anti-mouse isotype antibodies to various concentrations of mouse class and subclass specific immunoglobulins (Zymed Labs. Inc.).

The procedure used to determine antibody binding to specific sites of rapamycin and to quantify antibody cross-reactivity to FK-506, cyclosporine, and KLH or HSA proteins was as follows:

Inhibition ELISA Protocol

1. Use Falcon® Pro-bind™ inununoplates.
2. Dilute coating antigen to 1 μg/mL in carbonate-bicarbonate buffer.
Add 100 μL per well and incubate overnight at 4° C.
3. On the same day prepare inhibiting antigen tubes. Aliquot antibodies into glass test tubes. Prepare appropriate antigen concentration in ethanol and add to aliquoted antibody at 10 μL ethanol solution/250 μL antibody.
Vortex tubes and incubate overnight at 4° C.
4. Shake out wells and wash 3× with 200 μL PBS/0.05% TWEEN™ (polyoxyethylene-sorbitol) (v/v) per well.
5. Add 200 μL blocking buffer per well (PBS/2% BSA (w/v)).
Incubate 60 min at room temperature.
6. Wash as in step 4.
7. Transfer contents of inhibition tubes to antigen-coated plate, 100 μL per well. Incubate 60 min at 37° C.
8. Wash as in step 4.
9. Dilute alkaline phosphatase conjugated anti-mouse IgG (Tago cat # AMI 4405) in PBS/0.1% TWEEN™ (polyoxyethylene-sorbitol) (v/v) to 1:2000 concentration. Add 100 μL per well and incubate at 37° C. for 60 min.
10. Wash as in step 4.
11. Prepare enzyme substrate using Sigma # 104 alkaline phosphatase substrate tablets (1 mg/mL in 10% diethanolamine (v/v) substrate buffer). Add 100 μL per well and incubate in the dark at room temperature. Absorbance can be read at 405 nm at approximately 15-min intervals.

Buffers used in the direct, isotyping and inhibition ELISA protocols were:

| Coating buffer (sodium carbonate/bicarbonate 0.05 M. pH 9.6) | |
| --- | --- |
| Sodium carbonate (Fisher, cat # S-233-500) | 2.93 g |
| Sodium bicarbonate (Fisher, cat # S-263-500) | 1.59 g |
| adjust pH to 9.6 using 1 M HCl or 1 M NaOH | |
| store at 4° C. | |
| 10x PBS buffer | |
| Potassium phosphate, mono-basic (Fisher, cat P-284B-500) | 8.00 g |
| Sodium phosphate, di-basic (Fisher, cat # S-373-1) | 46.00 g |
| Sodium chloride (Fisher, cat # S-671-3) | 320.00 g |
| Potassium chloride (Fisher, cat # P-217-500) | 8.00 g |
| dissolve in 4 L distilled water | |
| store at room temperature | |
| Dilution buffer (1x PBS/0.1% Tween) | |
| 10x PBS | 50.0 mL |
| distilled water | 450 mL |
| TWEEN-20 ™ (Polyoxyethylene-sorbitol) monolaurate Sigma, cat # P-1379) | 0.5 mL |
| adjust pH to 7.2 and store at room temperature | |
| Wash buffer (1x PBS/0.05% Tween) | |
| 10x PBS | 200 mL |
| distilled water | 1800 mL |
| TWEEN-20 ™ (Polyoxyethylene-sorbitol monolaurate Sigma, cat # P-1379) | 1.0 mL |
| adjust pH to 7.2 and store at room temperature | |
| Blocking buffer (1x PBS/2% BSA) | |
| 1x PBS | 100 mL |
| Bovine Serum Albumin (Sigma, cat # A-7030) store at 4° C. | 2.0 g |
| Substrate buffer (10% diethanolamine) | |
| Diethanolamine (Fisher, cat # D-45-500) | 97.0 mL |
| Magnesium chloride (Fisher, cat # M-33-500) | 100.0 mg |
| adjust pH to 9.8 and store at 4° C. (protect from light) | |

The direct ELISA, isotyping and inhibition ELISA procedures have been described to detect mouse antibodies (poly- and monoclonal antibodies), however these procedures can be modified for other species, including but not limited to antibodies of rat, rabbit, chicken, guinea pig, donkey, pig, goat, cow, horse, dog, cat, monkey or baboon. Other procedures known in the art, including but not limited to various automated assay systems and RIA may be used to screen, characterize, test specificity and reactivity of poly- and/or monoclonal antibodies.

EXAMPLE 8

Polyclonal Antibody Responses to the Rapa-42-DVS Immunogen

Polyclonal antiserum was prepared in mice, chicken and rabbits using the Rapa-42 immunogen described in Example 1 and the immunization regimes described in Example 6. The ELISA reactivity of rabbit and chicken serum (7 days post-tertiary injection) to Rapa and FK-HSA conjugates is shown in Table 1.

TABLE 1

Rabbit and Chicken Polyclonal Antibody (Rapa-42-DVS-KLH Immunogen) Reactivity to Rapa and FK (O.D. at 405 mn).

| ELISA antigens | Rabbit #1 | Rabbit #2 | Chicken |
| --- | --- | --- | --- |
| Rapa-HSA | 1.634 | 2.528 | 1.537 |
| FK-HSA | 0.039 | 1.478 | 0.632 |
| HSA | 0.128 | 0.122 | 0.176 |

Rabbits # 1 and # 2 showed good antibody reactivity to the Rapa antigen with O.D.'s at 405 nm of 1.634 and 2.528 respectively. The serum dilution from rabbit # 1 showed low cross-reactivity to the FK antigen (2.3%) and low non-specific reactivity to the HSA carrier molecule (7.8%). The serum dilution from rabbit # 2 however, displayed substantial cross-reactivity with the FK antigen (58.5%), non-specific reactivity to the HSA carrier was low (4.8%).

The IgY recovered from eggs (PEG isolation method) of a Rapa immunized chicken had good reactivity to the Rapa antigen and showed a 41% cross-reactivity with the FK antigen. Non-specific reactivity to the HSA carrier was low at 11.5%.

The serum from rabbit # 1, having the best specificity to the Rapa antigen, was used in an inhibition ELISA assay, the results are shown in Table 2.

TABLE 2

Percent Inhibition of Rabbit and Chicken Polyclonal Antibodies by Rapa, FK, CSA, Rapa and FK Metabolites.

| Inhibiting antigens | Rabbit #1 | Chicken |
|---|---|---|
| Rapa | 48 | 30 |
| Met 1 | 18 | 34 |
| Met 2 | 22 | 0 |
| Met 3 | 15 | 35 |
| Met 4 | 28 | 18 |
| Met 5 | 16 | 35 |
| FK | 0 | 0 |
| Met 1 | 0 | 0 |
| Met 2 | 0 | 0 |
| Met 3 | 0 | 0 |
| Met 4 | 0 | 13 |
| Met 5 | 0 | 0 |
| CSA | 0 | 0 |
| KLH | 0 | 0 |
| HSA | 0 | 0 |

This serum was inhibited 48% by Rapa. Rapa metabolites 1–5 showed marginal inhibition from 15–28% (metabolite specificities listed in Table 3). CSA, FK or FK metabolites 1–5 showed no inhibition, the KLH and HSA proteins did not inhibit antibody binding to the Rapa antigen coated ELISA plate. The chicken IgY prep demonstrated less inhibition with Rapa or the five Rapa metabolites and no inhibition with FK, CSA, KLH or HSA proteins or four of the FK metabolites (FK metabolite # 4 showed a low level of inhibition).

TABLE 3

List of Rapamycin and FK Metabolites Used in Inhibition ELISA Assays

| | Functional Group Identification |
|---|---|
| Rapa Metabolites* | |
| M1 | Hydroxy Rapamycin (Hydroxylation is between C9 and C23) |
| M2 | Hydroxy Rapamycin (Hydroxylation is between C1 and C8 or C32 and C36) |
| M3 | 7-O-Demethyl Rapamycin |
| M4 | 41-O-Demethyl Rapamycin |
| M5 | 32,41-Demethyl Rapamycin |
| FK Metabolites** | |
| M1 | 13-O-Demethyl |
| M2 | 15-O-Demethyl |
| M3 | 31-O-Demethyl |
| M4 | 13,3 1-Didemethyl |
| M5 | 15,3 1-O-Didemethyl |

*Rapa metabolites were isolated by procedures described in Example 5.
**FK metabolites were isolated by procedures known in the art.

Balb/c female mice immunized (1°, 2°, 3° and 2 booster injections) with the Rapa-DVS-KLH immunogen (as described in Example 1) or with the Rapa-suc-KLH immunogen (as described in Example 2) showed good reactivity to the Rapa antigen (direct ELISA results shown in Table 4), with low non-specific reactivity to the HSA carrier molecule. However, the sera from mice immunized with the Rapa-suc-KLH immunogen showed high cross-reactivity with the FK antigen, displaying 92.5%, 57.4% and 60.2% FK cross-reactivity with sera from mouse # 1, 2 and 3, respectively. With sera from mice immunized with the Rapa-DVS-KLH immunogen, the FK cross-reactivity was much less, at only 11.6%, 33.4% and 6.7% for mice # 4, 5 and 6, respectively. These results demonstrate that the Rapa-DVS conjugates elicit Rapa-specific antibody, while the Rapa-suc conjugate elicits antibody with marked cross-reactivity to the FK antigen. Thus, the DVS conjugates of this invention are preferred for producing Rapa-specific antibodies.

Table 5 shows the sera reactivity from four Balb/c (Rapa-DVS-KLH immunogen; 1°, 2°, 3° and booster injections) mice used in fusion procedures of the invention. All four mice had good antibody levels (high O.D.'s by direct ELISA to Rapa-HSA) with little or no non-specific reactivity to the carrier protein HSA. As was shown with the results in Table 4, the cross-reactivity to the FK antigen was very low, mice 7, 8, 9 and 10 having only 12.4%, 13.9%, 15.6% and 19.9% FK cross-reactivity respectively. This result again demonstrates the utility of a DVS-immunogen for eliciting rapamycin specific antibodies. The Rapa-DVS immunogen elicited high titer antibody to the Rapa antigen, as demonstrated in Table 6 which shows that the Rapa-DVS mouse # 7 had substantial antibody reactivity to the Rapa antigen at a 1:800 serum dilution and that mouse #10 had good antibody reactivity to Rapa-antigen at a 1:6400 serum dilution.

TABLE 4

Mouse Polyclonal Antibody (Rapa-suc-KLH or Rapa-DVS-KLH Immunogens) Reactivity to Rapa and FK (O.D. at 405 nm).

| ELISA antigens | Rapa-suc #1 | Rapa-suc #2 | Rapa-suc #3 | Rapa-DVS #4 | Rapa-DVS #5 | Rapa-DVS #6 |
|---|---|---|---|---|---|---|
| Rapa-HSA | 1.518 | 1.817 | 1.781 | 1.891 | 1.808 | 1.606 |
| FK-HSA | 1.405 | 1.043 | 1.072 | 0.220 | 0.603 | 0.108 |
| HSA | 0.019 | 0.009 | 0.005 | 0.013 | 0.011 | 0.016 |

TABLE 5

Mouse Polyclonal Antibody Reactivity (Rapa-DVS-KLH immunogen pre-fusion bleeds) to Rapa and FK

| ELISA antigens | Rapa-DVS #7 | Rapa-DVS #8 | Rapa-DVS #9 | Rapa-DVS #10 |
|---|---|---|---|---|
| Rapa-RSA | 2.403 | 1.279 | 2.061 | 1.707 |
| FK-HSA | 0.298 | 0.179 | 0.322 | 0.340 |
| HSA | 0.033 | 0.006 | 0.050 | 0.010 |

TABLE 6

Titration of Mouse Polyclonal Sera to Rapamycin (O.D. at 405 nm)

| Dilution | Rapa-DVS#7 | Rapa-DVS#10 |
|---|---|---|
| 1:100 | 3.265 | 3.120 |
| 1:200 | 3.161 | 3.216 |
| 1:400 | 2.201 | 3.090 |
| 1:800 | 1.369 | 3.153 |
| 1:1600 | 0.674 | 2.635 |
| 1:3200 | 0.388 | 1.872 |
| 1:6400 | 0.219 | 1.090 |

Mouse polyclonal sera to the Rapa-DVS inmuunogen had little or no cross-reactivity to FK (confirming result in Table 5), CSA, KLH or HSA epitopes as demonstrated by inhibition ELISA results shown in Table 7. These sera showed significant inhibition with the Rapa antigen (approximately 50%) with varying levels of inhibition with the Rapamycin metabolites (M1–M5).

The results of Table 8 demonstrate that this inhibition was Rapa concentration dependent. Rapa significantly inhibited antibody binding at 2.5–0.15 μg concentrations, little inhibition was seen at the 0.04 μg Rapa concentration. The Rapa-HSA inhibitor showed a similar dose-dependent inhibition of anti-Rapa antibody binding. No inhibition occurred when HSA or KLH protein was used as inhibitor antigens in this assay.

TABLE 7

Percent Inhibition of Mouse Polyclonal Antibody by Rapa, FK, CSA and Rapa Metabolites

| Inhibiting antigens | Rapa-DVS #7 | Rapa-DVS #9 |
|---|---|---|
| Rapa | 50.8 | 45.6 |
| Met 1 | 29.1 | 34.9 |
| Met 2 | 14.0 | 27.4 |
| Met 3 | 28.3 | 30.8 |
| Met 4 | 40.1 | 28.6 |
| Met 5 | 39.8 | 37.3 |
| FK | 5.6 | 13.0 |
| CSA | 3.4 | 7.5 |
| KLH | 7.8 | 12.5 |
| HSA | 6.8 | 10.4 |

TABLE 8

Rapa Concentration Dependent Inhibition of Mouse Polyclonal Antibody (Rapa-DVS-KLH immunized pre-fusion bleed)

| Inhibiting Ag Concentration (μg) | Percent Inhibition Rapa | Percent Inhibition Rapa-42-HSA |
|---|---|---|
| 2.5 | 78 | 97 |
| 1.25 | 67 | 94 |
| 0.62 | 57 | 86 |
| 0.31 | 44 | 83 |
| 0.15 | 37 | 74 |
| 0.08 | 21 | 64 |
| 0.04 | 13 | 50 |

\* No inhibition with HSA or KLH

EXAMPLE 9

A Method for Monoclonal Antibody Production (MoAb)

The steps for monoclonal antibody production are summarized below:

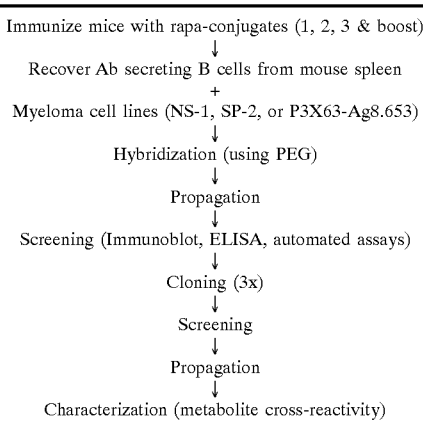

Immunize mice with rapa-conjugates (1, 2, 3 & boost)
↓
Recover Ab secreting B cells from mouse spleen
+
Myeloma cell lines (NS-1, SP-2, or P3X63-Ag8.653)
↓
Hybridization (using PEG)
↓
Propagation
↓
Screening (Immunoblot, ELISA, automated assays)
↓
Cloning (3x)
↓
Screening
↓
Propagation
↓
Characterization (metabolite cross-reactivity)
↓
Tissue culture MoAb production
↓
Ascites MoAb production The procedure used to produce the monoclonal antibodies of the invention is as follows:

Although there are many suitable reagent suppliers, we have found the following to be most preferred for obtaining a high yield of fusion products, for isolating stable clones and for the production of monoclonal antibodies (MoAb).

Dulbecco's Modified Eagles Medium (DMEM)
   from JRH BIOSCIENCES, Cat # 56499-10L+3.7 g/L NaHCO3 HAT supplement (100x–10 mM sodium hypoxanthine, 40 mM aminopterin, 1.6 mM thymidine)
   from CANADIAN LIFE TECHNOLOGIES, Cat # 31062-037 HT stock (100x–10 mM sodium hypozanthine, 1.0 mM thymidine)
   from CANADIAN LIFE TECHNOLOGIES, Cat # 11067-030 FCS
   CPSR-3 Hybrid-MAX from SIGMA, Cat # C.-9155 Poylethylene glycol (PEG)
   Use PEG 4000, SERVA # 33136. Autoclave PEG, cool slightly and dilute to 50% w/v with serum free DMEM. Make fresh PEG the day before the fusion, and place in 37° C. incubator.

Fusion Procedure:

Myeloma cells should be thawed and expanded one week before fusion and split the day before the fusion. Do not keep the myeloma cell line in continuous culture. This prevents the cells from becoming infected with mycoplasma and also from any changes, which may result from repeated passaging.

For Example:
   SP2/0 can be split back to $1 \times 10^4$ cells/mL, freeze at least $5 \times 10^6$ cells/vial
   NS-1 can be split back to $1 \times 10^4$ cells/mL, freeze at least $5 \times 10^6$ cells/vial
   P3X63-Ag8.653 can be split back to $1 \times 10^4$ cells/ml, freeze at least $5 \times 10^6$ cell/vial Culture the myeloma cell line so that you will have at least $0.5 \times 10^7$ cells (in log phase growth) on the day of the fusion. Three to five days prior to fusion, boost the immunized mouse. The mouse must be genotypically compatible with the myeloma cell line. Myeloma cell drug sensitivity should be confirmed.

Serum should be tested for its ability to support growth of the parental myeloma cell line. To test batches of serum, clone the parental myeloma cells (as outlined under cloning) in 10%, 5%, 2.5%, and 1% FCS. No feeder layer is required. Check growth and cell viability daily for 5 days.

Fusion Day
1. Place fresh medium, FCS to be used in fusion in water bath.
2. Harvest myeloma cells and wash 3× with serum-free medium (DMEM, RPMI or other commercially available tissue culture media may be used).
3. Remove spleen (lymph node cells may also be used) from immunized mouse; resterilize instruments or use new sterile instruments between each step, i.e. cutting skin, cutting abdominal muscle, removing spleen.
4. Rinse outside of spleen 3× by transferring to plastic petri plates containing sterile medium; use sterile forceps between each step.

5. Place spleen in plastic petri dish with serum-free medium in it, cut into 4 pieces and push gently through screen with sterile glass plunger to obtain a single cell suspension.
6. Centrifuge spleen cells in 50-ml conical centrifuge tubes at 300×g (1200 rpm in silencer) for 10 minutes.
7. Resuspend in 10-mL medium. Dilute an aliquot 100× and count cells.
8. Centrifuge rest of spleen cells, resuspend and recentrifuge. Myeloma cells can be washed at the same time. The NS-1, SP2/0 and P3X63Ag8 myeloma cell lines are most preferred, however other myeloma cell lines known in the art may be utilized. These include, but are not limited to, the mouse cell lines: X63Ag8.653, OF, NSO/1, FOX-NY; rat cell lines; Y3-Ag1.2.3, YB2/0 and IR983F and various rabbit and human cell lines.
9. Add myeloma and spleen cells together in 5:1 or 10:1 ratio with spleen cells in excess.
10. Recentrifuge: spleen cells and myeloma have now been washed 3×.
11. Gently flick pellet and place in incubator for 15 minutes to reach 37° C.

Fusion Protocol:
1. Add 1-ml of 50% PEG (w/v) solution over 1 minute stirring (add 0.25 mL1/15 sec) holding tube in 37° C. water bath (beaker with warm water). PEG fuses membranes of myeloma with antibody secreting (B) cells.
2. Stir 1-minute holding in 37° C. water bath. Solution will turn lumpy.
3. Add 1-ml medium at 37° C. over 1-minute stirring.
4. Add another mL medium over 1-minute stirring.
5. Add 8-mL medium over 2 minutes stirring.
6. Centrifuge for 10 minutes at 300×g (1200 rpm in silencer) and pipet off supernatant.
7. Add 10 mL medium+20% FCS (v/v) to cells in tube and pour into plastic petri dish.
8. Leave in incubator with 5% $CO_2$ at 37° C. for 1–3 hours. This enhances stability of fusion products.
9. Plate cells out at a concentration of $2 \times 10^5$ cells per well in medium (100 μl/well).
10. Feed cells 100 μl of 2× HAT in medium the next day. No feeder layer is necessary at this time
    Feed fusion products 100 μL medium+HAT selection additive on day 3. Hybridoma cells (myeloma:spleen cell hybrids) are selected by the addition of the drug aminopterin which blocks the de novo synthesis pathway of nucleotides. Myeloma:spleen hybrid cells can survive by use of the salvage pathway. Unfused myeloma cells and myeloma:myeloma fusion products have a defect in an enzyme of the salvage pathway and will die. Unfused spleen cells from the immunized mouse do not grow in tissue culture. Other drugs known in the art may be used to select myeloma:spleen cell hybrids, such as methotrexate or azaserine.
    Feed fusion products 100 μL medium+HAT+spleen/thymus feeder layer if necessary on day 5 ($1 \times 10^5$ cells/well). Fibroblasts, RBC's or other cell types may also be used as feeder layers.
    Continue to feed cells medium+HAT for 1 week, by day 7 post-fusion, change to medium+HT. Clones should appear 10–14 days after fusion.

Note:
1. Washing of the spleen cells, myeloma cells and steps 1–6 of the fusion protocol are performed with serum-free medium.
2. Thymocytes die in about 3 days, non-fused spleen cells in about 6 days.
3. Hybrids are fairly large and almost always round and iridescent.
4. T-cell and granulocyte colonies may also grow. They are smaller cells.

To Clone Hybrid Cells:
1. Resuspend the 200 μl in the well with a sterile eppendorf pipet tip and transfer to a small 5-mL sterile tube.
2. Add 200 μl medium (20% FCS v/v) to the original well. This is a safety precaution of the cloning procedure. Parent cells may also be transferred to 24 well plates as a precaution.
3. Take 20 μl of the hybrid cell suspension from step 1 and add 20 μl of eosin or trypan blue solution. Under 40× magnification hybrid cells appear to be approximately the same size and morphology as the myeloma cell line.
4. Clone viable cells by limiting dilution with:
   20% FCS (v/v) used in fusion medium
   1×HT
   $1 \times 10^6$ thymocytes per ml
   clone 1400 cels per cloning protocol Dilution Cloning Procedure:
Make 10 mL of thymocyte cloning suspension in DMEM with 20% FCS (v/v). Take 1440 hybrid cells and dilute to 2.8 mL.
   Row 1: Plate 8 wells (200 μl/well)→100 cells/well.
      To the remaining 1.2-mL add 1.2-mL medium.
   Row 2: Plate 8 wells (200 μL/well)→50 cells/well.
      To the remainder add 2.0-mL medium.
   Row 3: Plate 8 wells (200 μL/well)→10 cells/well
      To the remainder add 1.2-mL medium.
   Row 4: Plate 8 wells (200 μL well)→5 cells/well.
      To the remainder add 2.8-mL medium.
   Row 5 & 6: Plate 16 wells (200 μl/well)→1 cell/well.

After cloning and screening for positive wells, re-clone the faster growing, stronger reacting clones. To ensure that a hybridoma is stable and single-cell cloned, this cloning is repeated 3 times until every well tested is positive. Cells can then be grown up and the tissue culture supernatants collected for the monoclonal antibody. Other limiting dilution cloning procedures known in the art, single-cell cloning procedures to pick single cells, and single-cell cloning by growth in soft agar may also be employed.

Monoclonal Antibody Production:
Monoclonal antibodies can be readily recovered from tissue culture supernatants. Hybrid cells can be grown in tissue culture media with FCS supplements or in serum-free media known in the art. Large-scale amounts of monoclonal antibodies can be produced using hollow fiber or bioreactor technology. The concentration, affinity and avidity of specific monoclonal antibodies can be increased when produced as ascitic fluid.

Ascitic Fluid Production:
1. Condition mice by injecting (I.P.) 0.5-mL pristane (2, 6, 10, 14-tetramethypentadecane) at least 5 days before hybrid cell are injected. Mice should be genotypically compatible with cells injected, i.e., Balb/c mice should be used with NS-1 or SP2/0 fusion products. Mice of non-compatible genotype may be used if irradiated before cells are injected. However, Balb/c pristane treated mice are the best to use.
2. Inject (I.P.) $10^6$ (or more) hybrid cells in PBS. Wash cells 3× prior to injection to remove the FCS .
3. Mice will be ready to tap in about 7–14 days. Use an 18½ G needle to harvest ascites cells and fluid.
4. Transfer at least $10^6$ ascites cells from these mice to more pristane treated mice.
5. Ascites cells can be frozen in 10% DMSO (v/v), 20% FCS (v/v), DMEM medium. Freeze about $5 \times 10^6$ cells per vial.

Monoclonal antibodies prepared in tissue culture or by ascitic fluid may be purified using methods known in the art.

EXAMPLE 10

Isolation and Characterization of Monoclonal Antibodies to Specific Sites of Rapamycin The steps to isolate and characterize monoclonal antibodies with reactivity to a specific site(s) of rapamycin are outlined below:

Steps to Identify MoAb to Specific Sites of Rapamycin:

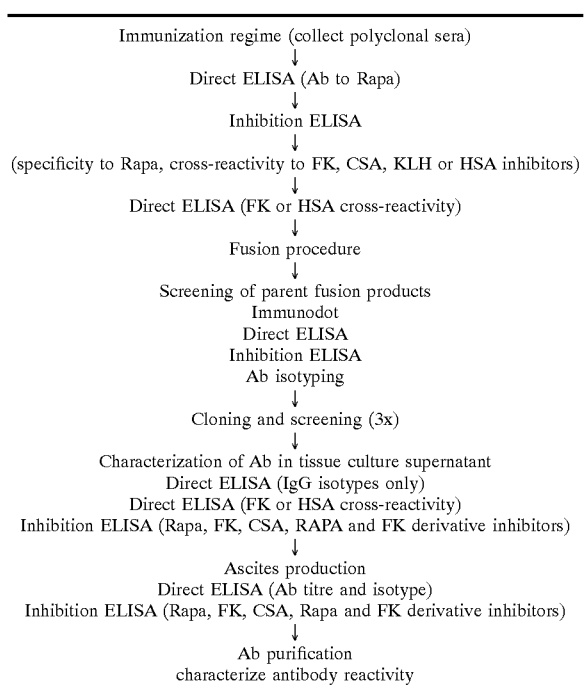

Parent fusion products from myeloma:spleen cells were initially screened by an immunodot assay as follows:

Immunodot Assay

1. Dot 5–10 μL of antibody onto nitrocellulose paper, which has been gridded for reference.
2. Air-dry and immerse nitrocellulose in PBS/0.1% TWEEN™ (polyoxyethylene-sorbitol) (v/v)/5% Milk (w/v) to block non-specific binding sites. Incubate at room temperature for 60 min with shaking.
3. Rinse twice with PBS/0.05% TWEEN™ (polyoxyethylene-sorbitol) (v/v) and wash with shaking for 10 min.
4. Dilute alkaline phosphatase conjugated anti-mouse IgG (Tago cat # AMI 4405) in PBS/0. 1% TWEEN™ (polyoxyethylene-sorbitol) (v/v) to 1:2000. Place nitrocellulose on parafilm or saran wrap and add diluted conjugated antibody until nitrocellulose is covered. Incubate covered at 37° C. for 60 min. Do not allow nitrocellulose to dry out between steps.
5. Wash as in step 3.
6. Prepare enzyme substrate using BCIP (5-bromo-4-chloro-3-indolyl phosphate)/NBT (nitrobenzyl tetrazolium) (Canadian Life Technologies, cat # 18280-016; 88 μL NBT and 66 μL BCIP in 20 mLs substrate buffer, 100 mM Tris, 5 mM $MgCl_2$, 100 mM NaCl). Place nitrocellulose in substrate solution and shake at room temperature for 10–30 min, watching for color development.
7. Rinse nitrocellulose with water to stop reaction.

Once antibody secreting parent fusion products were identified, the tissue culture supernatants were further characterized for rapamycin reactivity by the direct, isotyping and inhibition ELISA assays as described in Example 7. Various automated assays known in the art could also be utilized to screen parent fusion products. Tissue culture supernatants from clones (3×) of rapamycin positive parent fusion products were then characterized by isotyping ELISA to isolate IgG producing clones, by direct ELISA to determine FK and HSA cross-reactivity and by inhibition ELISA using Rapa, CSA, FK and Rapa and FX metabolites to determine specificity and rapamycin site reactivity. Automated assay systems could also be used to determine specificity and site reactivity.

Using the immunodot and direct ELISA assays over 600 parent fusion products were identified which have strong reactivity to the Rapa antigen. Of these parent products, over 200 have been cloned, tested for reactivity to Rapa by direct ELISA, and 100 positive clones were then re-cloned (2×). We have now isolated many IgM and IgG secreting clones with reactivity to the Rapa antigen by direct, inhibition and isotyping ELISA assays. Table 9 illustrates examples of ELISA reactivity using IgG monoclonal antibodies (Rapa-42-DVS-KLH immunogen) from clones of various fusion procedures (R-1, R-2 and R-3).

TABLE 9

Monoclonal Antibody (Rapa-42-DVS-KLH immunogen) Reactivity to Rapa, FK and HSA (O.D. at 405 nm)

| IgG Producing Clone #/ ref. name | Rapa-42-HSA | FK-32-HSA | FK Cross Reactivity (%) | HSA |
|---|---|---|---|---|
| R-1-1/1H3 | 1.929 | 0.899 | 46.6 | 0.005 |
| R-1-2/1D3-1 | 1.533 | 0.933 | 60.9 | 0.001 |
| R-1-3/1D3-2 | 1.581 | 1.041 | 65.8 | 0.002 |
| R-1-4/5C4 | 2.424 | 0.372 | 15.3 | 0.003 |
| R-1-5/2A10 | 0.654 | 0.117 | 17.9 | 0.001 |
| R-2-1/7H8 | 0.881 | 0.166 | 18.8 | 0.003 |
| R-2-2/8C3 | 3.122 | 0.037 | 1.2 | 0.036 |
| R-2-3/2H5 | 0.655 | 0.609 | 92.9 | 0.033 |
| R-2-4/3E5 | 0.535 | 0.298 | 55.7 | 0.027 |
| R-2-5-/1F7 | 1.603 | 1.151 | 71.8 | 0.001 |
| R-2-6/7H1 | 0.440 | 0.116 | 26.4 | 0.001 |
| R-3-1/7G1 | 2.825 | 0.002 | 0.1 | 0.005 |
| R-3-2/11B8 | 0.579 | 0.003 | 0.5 | 0.002 |

The monoclonal antibody reactivity to the Rapa-42 antigen varies from 0.440 to 3.122 O.D. units in these 13 examples. Non-specific reactivity to the carrier HSA protein is negligible. Monoclonal antibody cross-reactivity to the FK antigen of these clones varies considerably. The clones R-1-4, R-1-5, R-2-1, R-2-2, R-2-6, R-3-1 and R-3-2 show little or only marginal binding to the FK antigen; clones R-1-1 and R-2-4 have approximately 50% cross-reactivity to the FK antigen; clones R-1-2, R-1-3 and R-2-4 show significant cross-reactivity to FK and clone R-2-3 demonstrates almost equivalent affinity and reactivity for the FK and Rapa antigens. For development of therapeutic drug monitoring assays (TDM) with specificity for Rapa, the clones secreting antibodies with low or little cross-reactivity to the FK antigen would be preferred. Most preferred would be clones which secrete high levels of anti-Rapa IgG monoclonal antibodies with a low level of anti-FK cross-reactivity. Examples of such clones listed in Table 9 would be R-1-4, R-2-2 and R-3-1.

EXAMPLE 11

Mapping of anti-Rapa-42 Monoclonal Antibody Binding Region

To further characterize the reactivity of monoclonal antibodies from various clones, inhibition ELISA were performed. Table 10 shows example inhibitions from monoclonal antibodies of 4 clones. The monoclonal antibody from the R-1-1 clone is significantly inhibited by Rapa (85%) and by Rapa metabolite # 2 (77%). The antibody binding is not inhibited by Rapa metabolite # 1(15%) and moderately inhibited by Rapa metabolites #3, #4 and #5 (32%, 30% and 29% respectively). The mapping of reactivity of this monoclonal antibody with the metabolite M1–5 inhibitors, would indicate that the specific site for antibody binding is between C9 and C23. Hydroxylation in metabolite #1 between C9 and C23 changed a significant epitope in this region # 3–5 is most probably due to conformational changes of the parent Rapamycin molecule with demethylation of residues 7, 32 and 41. This monoclonal antibody was found to be 46% cross-reactive with the FK antigen by direct ELISA. The binding of R-1-1 MoAb was also found to be cross-reactive with FK by inhibition ELISA, where FK inhibited antibody binding by 43%. FK metabolites also significantly inhibited (43–57%). Cross-reactivity with FK and FK metabolites further confirms the antibody recognition site is in the C9–C23 region, as the FK and Rapa molecules are structurally similar in that region. CSA, KLH or HSA proteins showed no inhibition.

With the R-1-5 MoAb, Rapa and Rapa metabolite # 2 significantly inhibited antibody binding. There was no inhibition with the Rapa metabolite # 1, again suggesting that the specific site of this anti-Rapa antibody is located in the C9 to C23 region. The inhibition noted with Rapa metabolites #3–5 is again believed to be due to conformational changes in the antibody binding site caused by demethylation of residues 7, 32 and 41. This monoclonal showed some cross-reactivity with the FK antigen, a cross-reactivity that was also observed with all FK metabolites. Cross-reactivity to FK antigen as measured by direct ELISA was only marginal (Table 9). The R-1-5 MoAb did not bind to CSA, KLH or HSA proteins.

Chemical derivatization of specific sites on the rapamycin molecule including the carbon residues, nitrogen residues, oxygen, hydroxy, methoxy or methy groups will produce compounds similarly useful as the above metabolites for mapping the antibody binding region.

TABLE 10

Percent Inhibition of MoAb Tissue Culture Supernatents by Rapa, FK, CSA and Rapa and FK Metabolites

| Inhibiting Antigen | R-1-1 | R-1-5 | R-2-2 | R-3-1 |
|---|---|---|---|---|
| Rapa | 85 | 77 | 83 | 98 |
| Rapa met 1 | 15 | 12 | 16 | 38.2 |
| Rapa met 2 | 77 | 91 | 88 | 95 |
| Rapa met 3 | 32 | 56 | 26 | 92 |
| Rapa met 4 | 30 | 57 | 71 | 96 |
| Rapa met 5 | 29 | 44 | 10 | 94 |
| FK | 43 | 33 | 16 | 1 |
| FK met 1 | 46 | 24 | 19 | 0 |
| FK met 2 | 57 | 36 | 16 | 0 |
| FK met 3 | 45 | 26 | 9 | 0 |
| FK met 4 | 53 | 38 | 13 | 0 |
| FK met 5 | 46 | 26 | 13 | 0 |
| CSA | 6 | 0 | 0 | 0 |
| KLH | 3 | 10 | 16 | 0 |
| HSA | 2 | 10 | 16 | 0 |

Rapa and Rapa metabolite # 2 inhibited R-2-2 MoAb binding to Rapa antigen coated ELISA plates. Rapa metabolites # 1, #3 and #5 did not significantly inhibit binding, however metabolite # 4 showed significant inhibition at 71%. We believe that this might indicate that the MoAb's binding site is again in the C9 to C23 region, that a modification of this region affects binding (as observed with metabolite # 1), and that demethylation at site 41 also affects antibody binding due to conformational changes within the antibody site. The fact that metabolites #3 and #5 have less inhibitory effect than with MoAbs R-1-1 and R-1-5, may be due to a greater affinitys of MoAb R-2-2 for the antibody binding site (specific antibody epitope) or possibly that the R-2-2 MoAb recognizes a slightly different antibody binding epitope in the C9–C23 region than the R-1-1 or R-1-5 MoAbs.

Indeed, tissue culture supernatants of R-2-2 showed the highest O.D. reactivity with the Rapa antigen by direct ELISA (Table 9) indicating good antibody affinity/avidity. The fact that R-2-2 MoAb showed very little cross-reactivity with FK or FK metabolites 1–5 again indicates good affinity/avidity with the specific antibody binding site on Rapamycin. Even though the FK and Rapamycin molecules are structurally similar at the nitrogen ring region (chemical structure), studies indicate there are conformational differences between these molecules. Three dimensional structure plays an important role in epitope presentation and recognition by the immune system, therefore a MoAb with high affinity, avidity and specificity for a specific three dimensional epitope site of Rapamycin, would not necessarily cross-react with molecules of similar chemical structure, such as FK.

R-2-2 did not react with CSA, KLH or HSA.

With the R-3-1 MoAb, Rapa and Rapa metabolites #2–5 significantly inhibited antibody binding to sites on the Rapa molecule. Rapa metabolite # 1 marginally inhibited antibody binding (38%) and FK and FK metabolites #1–5, CSA, KLH or HSA showed no inhibition to this MoAb's specific site on Rapa. Again these results could suggest that the specific antibody binding epitope may be in the C9–C23 region, however unlike previous monoclonal antibody epitope mapping results, the demethylation (M3, 4, 5) did not reduce inhibiting capacity (i.e. inhibited similar to the parent Rapa molecule). We believe that R-3-1 may recognize an epitope in the C9–C23 region, or alternately recognize an epitope in the opposite face of the molecule, for example between, C24–C36. Identification of the specific site of R-3-1 on the Rapa molecule can be done using various other minor metabolite peaks isolated as described in Example 5.

A further clue that R-3-1 may recognize a different binding site than R-1-1, R-1-5 or R-2-2 was elucidated from results of experiments using various dilution buffers in our inhibition assay. We observed that Rapamycin which had been diluted in only aqueous buffer did not inhibit the binding of MoAbs R-1-1, R-1-5 or R-2-2, while Rapamycin diluted in aqueous buffer containing 10% FCS (v/v) did inhibit binding, possibly indicating that a modification to Rapamycin, such as hydrolysis in aqueous buffer, modifies the antibody binding site and no longer binds the MoAbs. Rapamycin maintained in a buffer less likely to cause hydrolysis (i.e. aqueous buffer containing 10% FCS (v/v)), would maintain antibody binding epitope integrity and bind MoAbs R-1-1, R-1-5 or R-2-2. MoAb R-3-1 was inhibited by Rapamycin diluted in either aqueous buffer or aqueous buffer containing 10% FCS (v/v). This finding indicates that MoAb R-3-1 recognizes a specific site of Rapamycin which is not affected by hydrolysis, a site different from the hydrolysis-sensitive binding site of MoAbs R-1-1, R-1-5 and R-2-2.

EXAMPLE 12

Isolation of Monoclonal Antibodies to Rapamycin (Rapa-42-DVS-KLH immunogen) Derived from Spleen Cells of Hyperimmunized Mice To increase affinity/avidity of monoclonal antibodies, mice were immunized (1°, 2°, and 3°) as described in Example 6, and then administered several monthly boosters. Numerous additional clones were derived using this immunization procedure.

The reactivity of MoAbs from representative clones to an antigen panel is shown in Table 11. These clones react strongly with the Rapa-42-HSA and Rapa-27-HSA antigens and show no cross-reactivity with FK, CSA or HSA. These MoAbs do not recognize epitopes on the FK molecule (as tested by antigen panel ELISA) and appear to show good specificity for rapamycin. ELISA titration of R-4-1, R-4-7 and R-5-3 purified MoAbs to the Rapa-42 and Rapa-27-HSA conjugates is shown in FIGS. 2A–2C. The R-4-1 and R-5-3 MoAbs have high titers and reactivity to epitopes of the Rapa-42 and Rapa-27-HSA conjugates, while the MoAb R-4-7 shows less reactivity to the Rapa-27-HSA than Rapa-42-HSA conjugate. A similar reduction in reactivity to Rapa-27-HSA was observed with R-4-7 tissue culture supernatant (Table 11). These MoAbs are inhibited by rapamycin and by RAD, a 42-0-(2-hydroxy-ethyl) derivative of Rapa[7]. FIGS. 3A and 3B show the inhibition ELISA results of purified R-4-1 and R-5-3 MoAbs with increasing concentrations of Rapa or RAD. These MoAb clones appear to have marginally greater reactivity and affinity for Rapa than RAD. FIG. 4 shows inhibition ELISA results of MoAb R-5-3 inhibited by a 0–15 ng range of rapamycin.

TABLE 11

Reactivity of MoAbs R-4-1, R-4-7 and R-5-3 (Rapa-42-KLH immunogen) to Rapa, FK, CSA and HSA ELISA Antigen Panel

| IgG Producing Clone#/ Ref. Name | Rapa-42-HSA | Rapa-27-HSA | FK-32-HSA | CSA-HSA | HSA |
|---|---|---|---|---|---|
| R-4-1/3E10 | 3.364 | 3.464 | 0.088 | 0.094 | 0.085 |
| R-4-7/6C7 | 3.245 | 1.099 | 0.097 | 0.090 | 0.082 |
| R-5-3/8BP | 3.507 | 3.286 | 0.111 | 0.093 | 0.085 |

Inhibition ELISA's were performed using MoAb tissue culture supernatants from R-4-1, R4-7 and R-5-3 to map the antibody region (Table 12).

TABLE 12

Percent Inhibition of MoAb Tissue Culture Supernatants by Rapa, Rapa Metabolites, FK and CSA

| Inhibiting Antigen | R-4-1 | R-4-7 | R-5-3 |
|---|---|---|---|
| Rapa | 88 | 71 | 69 |
| Rapa M1 | 83 | 41 | 72 |
| Rapa M2 | 32 | 17 | 10 |
| Rapa M3 | 85 | 67 | 37 |
| Rapa M4 | 82 | 54 | 47 |
| Rapa M5 | 88 | 87 | 46 |
| FK | 8 | 4 | 4 |
| CSA | 8 | 0 | 10 |
| HSA | 2 | 6 | 13 |

The monoclonal antibodies from R-4-1, R-4-7 and R-5-3 clones are significantly inhibited by Rapa and do not cross-react with FK or CSA epitopes. These MoAbs have varied binding activity to the hydroxy Rapa metabolite M1 and the M3, M4 and M5 demethylated Rapa Metabolites but exhibit a significant reduction in binding activity to the M2 hydroxy metabolite. This indicates that the antibody binding site of these MoAbs may be in the M2 modified region, C1–C8 or C32–C36.

These MoAbs can be used to develop TDMs to determine rapamycin or RAD levels in patient samples. MoAb dilutions can be optimized to measure patient peak or trough drug levels or for monitoring drug levels in the therapeutic range (0–60 μg/L). The MoAbs of this invention can be used for therapeutic drug monitoring of patient samples in immunoassays or automated assay systems.

The poly- and monoclonal antibodies elicited to the Rapa-42-DVS-KLH immunogen of this invention can be used for development t of immunoassays or TDM tests to measure parent drug (Raga or RAD) levels. Such assays could include, but not limited to, direct, inhibition, competitive or sandwich immunoassays (ELISA or other assay systems), RIA, solid or liquid phase assays or automated assay systems.

EXAMPLE 13

Mouse Polyclonal Antibody Responses to the Rapa-27-ox-DVS Immunogen

Serum from Balb/c mice post-tertiary immunization with the Rapa-27-ox-DVS-KLH immunogen (as in Example 3) was tested for ELISA reactivity to Rapa-42-HSA, Rapa-27-HSA and FK-HSA (Table 13). These results indicate that serum from mice immunized with the Rapa-ox conjugate may recognize a different epitope on the parent rapamycin molecule than serum from mice immunized with the Rapa-42 conjugate. Anti-Rapa-27 serum reacts strongly with Rapa-27-HSA, but generally shows decreased and variable cross-reactivity with Rapa-42-HSA (12–63%), Table 13.

Inhibition ELISA data (Table 14) demonstrated that the parent Rapa molecule blocked anti-Rapa-27 antibody binding to Rapa-27-HSA (93%); CSA, KLH and HSA showed no inhibition. Rapa metabolite # 1 showed significant inhibition at 69%, indicating that the C9–C23 region of the molecule was not involved with antibody recognition. Hydroxylaiion in the region between C1–C8 or C32–C36 (metabolite #2) caused significant loss of inhibiting activity (inhibition only 36%), indicating that this region may play a role in antibody recognition. The inhibition observed with the parent molecule was decreased with demethylation at residues 7 and 41 (metabolites # 3 and # 4) from 93% to 42% and 37% respectively. Rapa metabolite # 5 (demethylated at residues 32 and 41) completely abrogated antibody binding to the parent molecule. This demonstrates that demethylation of the 32, 41 sites completely inhibit antibody binding to the epitope recognition site. However, as demethylation at the 41 site (metabolite # 4) or hydroxylation between the C1–C8 or C32–C36 did not completely inhibit antibody binding, we postulate that the methyl group at the 32 site may play a significant role in maintaining the three dimensional structure of the antibody binding epitope recognition site. The reduction in inhibiting capacity seen with metabolites #3 and #4 may be due to three-dimensional conformational changes with the antibody binding site.

TABLE 13

Mouse Polyclonal Antibody Reactivity (Rapa-27-ox-DVS-KLH immunogen) to Rapa and FK (O.D. at 405 nm)

| ELISA antigen | Rapa-27 #11 | Rapa-27 #12 | Rapa-27 #13 | Rapa-27 #14 | Rapa-27 #15 | Rapa-27 #16 | Rapa-27 #17 | Rapa-27 #18 |
|---|---|---|---|---|---|---|---|---|
| Rapa-27-HSA | 2.512 | 2.733 | 1.592 | 2.002 | 1.891 | 1.769 | 1.287 | 0.813 |
| Rapa-42-HSA | 1.594 | 0.490 | 0.605 | 0.968 | 0.235 | 0.817 | 1.538 | 0.398 |
| FK-HSA | 0.332 | 0.091 | 0.092 | 0.094 | 0.011 | 0.092 | 0.070 | 0.045 |
| HSA | 0.257 | 0.071 | 0.066 | 0.061 | 0.03 | 0.029 | 0.002 | 0.004 |

TABLE 14

Percent Inhibition of Mouse Polyclonal Antibody (Rapa-27-ox-DVS-KLH immunogen) by Rapa, FK, CSA and Rapa Metabolites

| Inhibiting antigens | Rapa-27 #12 |
|---|---|
| Rapa | 93 |
| Met 1 | 69 |
| Met 2 | 38 |
| Met 3 | 43 |
| Met 4 | 37 |
| Met 5 | 0 |
| FK | 11 |
| CSA | 0 |
| KLH | 0 |
| HSA | 0 |

EXAMPLE 14

Monoclonal Antibodies to the Rapa-27-ox-DVS-KLH Immunogen

Several monoclonal antibody clones derived from spleen cells of hyperimmunized mice with the Rapa-27-ox-DVS-KLH immunogen have been isolated. The ELISA reactivity of representative clones to a Rapa, FK, CSA and HSA antigen panel is shown in Table 15.

TABLE 15

Reactivity of MoAbs R-6-1, 2, 3 and 4 (Rapa-27-KLH immunogen) to Rapa, FK, CSA and HSA ELISA Antigen Panel

| IgG Producing Clone#/ Ref. name | Rapa-27-HSA | Rapa-42-HSA | FK-32-HSA | CSA-HSA | HSA |
|---|---|---|---|---|---|
| R-6-1/4G2 | 2.178 | 0.127 | 0.151 | 0.103 | 0.095 |
| R-6-2/8B4 | 3.426 | 0.657 | 3.234 | 0.159 | 0.103 |
| R-6-3/11A4 | 2.407 | 0.123 | 3.267 | 0.121 | 0.090 |
| R-64/14H10 | 3.454 | 0.461 | 3.306 | 0.139 | 0.116 |

Clones R-6-1,2,3 and 4 all showed strong binding to the Rapa-27-HSA with negligible binding to the Rapa42-HSA conjugates. The R-6-1 clone did not cross-react with FK, the R-6-2,3 and 4 clones showed strong cross-reactivity with the FK-32-HSA conjugate. No clones cross-reacted with CSA or HSA. Table 16 shows the ELISA titration of R-6-2 and R-6-4 MoAb to the Rapa-27-HSA conjugate.

TABLE 16

ELISA Titration of R-6-2 and R-6-4 MoAbs to Rapa-27-HSA Conjugate

| | O.D. at 405 nm | |
|---|---|---|
| TCS Dilution | MoAb R-6-2 | MoAb R-6-4 |
| neat | 3.246 | 3.247 |
| 1:2 | 3.372 | 2.931 |
| 1:4 | 3.083 | 2.775 |
| 1:8 | 3.598 | 3.180 |
| 1:16 | 3.523 | 3.011 |
| 1:32 | 3.376 | 2.857 |
| 1:64 | 3.375 | 2.561 |
| 1:128 | 3.026 | 2.654 |
| 1:256 | 2.930 | 2.460 |
| 1:512 | 2.460 | 1.520 |
| 1:1024 | 2.339 | 0.968 |
| 1:2048 | 1.757 | 0.982 |
| 1:4096 | 1.447 | 0.683 |
| 1:8192 | 1.091 | 0.532 |
| 1:16384 | 0.638 | 0.389 |
| 1:32768 | 0.394 | 0.277 |

The inhibition ELISA results in Table 17 further demonstrates MoAb cross-reactivity to the FK moiety. These MoAbs also bind the RAD moiety.

TABLE 17

Percent Inhibition of R-6-2 and R-6-3 MoAbs

| Inhibiting Antigens | R-6-2 | R-6-3 |
|---|---|---|
| Rapa | 71 | 66 |
| RAD | 70 | 58 |
| CSA | 0 | 0 |
| FK | 64 | 53 |
| HSA | 0 | 0 |

The data in this example indicates that the R-6-1 MoAb is specific for the Rapa-27 epitope and does not cross-react with Rapa-42, FK-32 or CSA epitopes. The R-6-2, 3 and 4 MoAbs are specific for Rapa and cross-react with the RAD and FK moieties. They do not cross-react with the CSA molecule.

In one aspect of the invention, the Rapa42-DVS conjugate (Example 1) may be utilized to elicit poly- or monoclonal antibodies to one region of rapamycin, and the Rapa-27-oxime-DVS conjugate (Example 3) or Rapa-31-DVS conjugate (Example 4) to elicit poly- or monoclonal antibodies to other regions of the rapamycin parent molecule. With such antibodies an immunoassay to measure rapamycin, RAD, and/or metabolites may be developed. Most preferred would be a TDM assay to specifically measure biologically active rapamycin molecules. Poly- and monoclonal antibodies with reactivity to various specific sites of rapamycin can be elicited with the conjugates of the invention.

EXAMPLE 15

Measuring the Biological Activity of Rapamycin and Rapamycin Metabolites by in vitro Mixed Lymphocyte Reaction (MLR) Assay The MLR assay is useful for identifying rapamycin metabolites with biological (immunosupressive) activity and to quantify this activity relative to the immunosuppressive activity of the parent rapamycin molecule.

An example of a two-way lymphocyte proliferation assay procedure useful for this purpose is as follows:

1. Collect blood from two individuals (20 mls each) and isolate lymphocytes using Ficoll-Paque™ (polysucrose and sodium diatrizoate) (Pharmacia Biotech).
2. Count lymphocytes at 1:10 dilution in 2% acetic acid (v/v).
3. Prepare 10 mls of each lymphocyte populations (A+B) at 1×10$^6$ cells/ml in DMEM/20% FCS (v/v).
4. Set up a 96 well sterile tissue culture plate, flat bottom (Sarstedt, cat # 83.1835). To each well add:
5. Aliquot 100 μl per well lymphocyte population A
6. Aliquot 100 μl per well lymphocyte population B
7. Aliquot 20 μl per well of drug (rapamycin and rapamycin metabolites M1–5) serially diluted 0 to 1000 μg/L in triplicate in DMEM with no supplements.
8. To measure the effect of drug on proliferation, incubate the plate for 5 days at 37° C. in 5% $CO_2$ atmosphere.
9. On day 6, prepare 3.2 mls of 1:50 dilution of Methyl-$^3$H-Thymidine (Amersham Life Science, cat # TRK 120) in DMEM with no supplements. Add 30μl per well incubate for 18 hours at 37° C. in 5% $CO_2$ atmosphere.
10. On day 7 cells are harvested onto glass microfiber filters GF/A (Whatman, cat # 1820024) using a Cell-Harvestor (Millipore, cat # XX2702550). Wash cells 3× with 1.0-ml sterile distilled water.

Note: All procedures are done using sterile techniques in a biological flow hood.

11. Place filters in Scintillation vials and add 1.5 mls of ScintiSafe Plus™ 50% scintillation fluid (Fisher, cat #SX-25-5).
12. Measure the amount of radioactivity incorporated in the lymphocytes using a beta counter (Micromedic System Inc., TAURUS™ Automatic Liquid Scintillation Counter) for 1.0 minute.
13. Calculate averages and standard deviations for each drug and express results as:

$$\% \text{ Inhibition} = \left[\frac{1 - \text{Ave CPM of test drug}}{\text{Ave CPM of zero drug}}\right] \times 100$$

The $IC_{50}$ values of Rapa and M1–M5 is shown in Table 18. The parent drug has a mean $IC_{50}$ value of 0.48 μg/L. The demethylated metabolites (M3–5) had $IC_{50}$ values of 5 to 10 times greater, indicating relatively low immunosuppressive activity. The hydroxy metabolites (M1, M2) have insignificant immunosuppressive activity. Table 19 shows the relative concentrations of these metabolites in pooled whole blood patient samples (determined by LC/MS). No individual metabolite is found at a concentration greater than 20% of the Rapa parent level.

TABLE 18

Mixed Lymphocyte Reaction $IC_{50}$ Values

| Compound | Mean (μg/L) | Range (μg/L) |
| --- | --- | --- |
| M-1 (C9–C23) | 467 | 180–800 |
| M-2 (C1–C8 OR C32–C36) | 252 | 140–380 |
| M-3 (7-O-Demethyl) | 2.85 | 2.0–4.5 |
| M-4 (41-O-Demethyl) | 5.9 | 3.2–7.7 |

TABLE 18-continued

Mixed Lymphocyte Reaction $IC_{50}$ Values

| Compound | Mean (μg/L) | Range (μg/L) |
| --- | --- | --- |
| M-5 (32,41-O-Demethyl) | 4.67 | 1.8–7.1 |
| rapamycin | 0.48 | 0.18–0.7 |

TABLE 19

Relative Concentrations of Rapa Metabolites in Whole Blood

| Compound | Relative Concentration |
| --- | --- |
| Rapa | 1 |
| M-1 (C9–C23) | 0.2 |
| M-2 (C1–C8 OR C32–C36) | 0.2 |
| M-3 (7-O-Demethyl) | 0.10 |
| M-4 (41-O-Demethyl) | 0.10 |
| M-5 (32,41-O-Didemethyl | 0.02 |

The MLR assay can be utilized to select antibodies of the invention which bind biologically active Rapa metabolites and the parent Rapa molecule. Antibodies could to also be selected for reactivity to biologically inactive metabolites.

EXAMPLE 16

Immunoassay Kits Using Polyclonal and Monoclonal Antibodies to Specific Sites of Rapamycin The polyclonal and monoclonal antibodies to specific sites of rapamycin of the invention may be used for development of immunoassays or TDM kits. Such assays could include, but are not limited to, direct, inhibition, competitive or sandwich immunoassays (ELISA or other assay systems), RIA, solid or liquid phase assays or automated assay systems.

As will be seen from the foregoing examples, procedures not described in detail are conventional. Variations and modifications will be apparent to those skilled in the art and are intended to be encompassed by the above descriptions and the claims appended hereto.

REFERENCES

The following references are referred to in this application by the use of superscript numbers.

1. Sehgal S. N., H. Baker C. Vezina. Rapamycin (AY-22, 989), A New Antifungal Antibiotic: II. Fermentation, Isolation and Characterization. J. Antibiot. (Tokyo) 28:727-732.
2. Streit F., Christians U., Schiebel H. M., Meyer A., Sewing K. F. Structural Identification of Three Metabolites and a Degradation Product of the Macrolide Immunosuppressant Sirolimus (Rapamycin) by Electrospray-MS/MS after Incubation with Human Liver Microsomes. Drug Metab Dispos. 24:1272, 1996.
3. Wang P. C., Lim H. K., Chan K. W. Isolation of Ten Metabolites from the Bile of Rats Receiving Rapamycin (Sirolimus) Intravenously. ISSX Proc. 8:1995.
4. Nickmilder M. J. M., Latinne D., Verbeeck R. K., Janssens W., Svoboda D., Lhoest G. .J. J. Isolation and Identification of New Rapamycin Dihydrodiol Metabolites from Dexamethasone Induced Rat Liver Microsomes. Xenobiotica 27:869, 1997.

5. Streit F., Christians U., Schiebel H. M., Napoli K. L., Ernst L., Linck A., Kahan B. D., Sewing K. F. Sensitive and Specific Quantitation of Sirolimus (Rapamycin) and its Metabolites in Blood of Kidney Graft Recipients by HPLC/Electrospray-Mass Spectrometry. Clin Chem. 42:1417, 1996.

6. Leung L. Y., Zimmerman J., Lim H. K., DiCioccio T. A., Warner L., Hicks D., Chan K., Kantrowitz J., Scatina J., Sisenwine S F, Tonelli A P. Metabolic Disposition of [14C]-Rapamycin (Sirolimus) in Healthy Male Subjects After Single Oral Dose. ISSX Proc. 12: 26, 1997.

7. Schuler W., Sedrani R., Cottens S., Haberlin B., Schulz M., Schuurman H- J., Zenke G., Zerwes H- G., Schreier M. H. SDZ RAD, A New Rapamycin Derivative. Transplant. 64:36, 1997.

The disclosure of each of the above publications, patents, and patent applications is incorporated herein by reference in its entirety.

What is claimed is:

1. A method for producing an antibody to a rapamycin compound selected from the group consisting of rapamycin and rapamycin metabolites, said antibody raised against an immunogen comprising the rapamycin compound conjugated to a protein carrier by a divinyl sulfone linker arm molecule, said method comprising:

a) administering said immunogen to an animal so as to effect a specific antibody response to the rapamycin compound;

b) recovering an antibody to said rapamycin compound from said animal; and c) measuring the reactivity of the antibody to said rapamycin compound, wherein the antibody specifically recognizes a region of said rapamycin compound which is located between C9 and C23.

2. The method of claim 1 wherein said protein carrier is selected from the group consisting of keyhole limpet hemocyanin and human serum albumin.

3. The method of claim 1 wherein said rapamycin compound is linked to the protein carrier at the 27, 31, 41 or 42 position of said rapamycin compound.

4. The method of claim 1 wherein said animal is a mouse, rat, rabbit, chicken, guinea pig, donkey, pig, goat, sheep, cow, horse, dog, cat or monkey.

5. The method of claim 1, wherein said rapamycin compound is a rapamycin metabolite.

6. The method of claim 5, wherein said rapamycin metabolite is selected from the group consisting of M1, M2, M3, M4, and M5.

7. The method of claim 1, wherein said rapamycin compound is rapamycin.

8. The method of claim 1 wherein step b) comprises recovering at least one antibody-producing cell from said animal, immortalizing said antibody-producing cell and isolating the antibody from said immortalized antibody-producing cell.

* * * * *